US008551136B2

(12) United States Patent
Lu

(10) Patent No.: US 8,551,136 B2
(45) Date of Patent: *Oct. 8, 2013

(54) HIGH SWELL, LONG-LIVED HYDROGEL SEALANT

(75) Inventor: Helen S. M. Lu, Wallingford, PA (US)

(73) Assignee: Actamax Surgical Materials, LLC, Berkeley, CA (US)

( * ) Notice: Subject to any disclaimer, the term of this patent is extended or adjusted under 35 U.S.C. 154(b) by 523 days.

This patent is subject to a terminal disclaimer.

(21) Appl. No.: 12/497,732

(22) Filed: Jul. 6, 2009

(65) Prior Publication Data

US 2010/0016886 A1 Jan. 21, 2010

Related U.S. Application Data

(60) Provisional application No. 61/135,173, filed on Jul. 17, 2008.

(51) Int. Cl.
*A61B 17/03* (2006.01)

(52) U.S. Cl.
USPC .................. 606/213; 106/217.6; 523/118

(58) Field of Classification Search
None
See application file for complete search history.

(56) References Cited

U.S. PATENT DOCUMENTS

| | | | |
|---|---|---|---|
| 4,542,176 A * | 9/1985 | Graham | 524/543 |
| 4,584,188 A | 4/1986 | Graham | |
| 4,703,116 A | 10/1987 | Solarek et al. | |
| 4,731,162 A | 3/1988 | Solarek et al. | |
| 4,741,804 A | 5/1988 | Solarek et al. | |
| 4,749,800 A | 6/1988 | Jobe et al. | |
| 4,766,245 A | 8/1988 | Larkin et al. | |
| 5,092,883 A | 3/1992 | Eppley et al. | |
| 5,116,824 A | 5/1992 | Miyata et al. | |
| 5,162,430 A | 11/1992 | Rhee et al. | |
| 5,196,441 A | 3/1993 | Kunisch et al. | |
| 5,275,838 A | 1/1994 | Merrill | |
| 5,292,802 A | 3/1994 | Rhee et al. | |
| 5,308,889 A | 5/1994 | Rhee et al. | |
| 5,324,775 A | 6/1994 | Rhee et al. | |
| 5,328,995 A | 7/1994 | Schaulin et al. | |
| 5,451,398 A | 9/1995 | Vigh | |
| 5,502,042 A | 3/1996 | Gruskin et al. | |
| 5,505,952 A | 4/1996 | Jiang et al. | |
| 5,514,379 A | 5/1996 | Weissleder et al. | |
| 5,567,685 A | 10/1996 | Linden et al. | |
| 5,643,575 A | 7/1997 | Martinez et al. | |
| 5,733,563 A | 3/1998 | Fortier | |
| 5,830,986 A | 11/1998 | Merrill et al. | |
| 5,840,698 A | 11/1998 | Campbell et al. | |
| 5,843,865 A | 12/1998 | Del Corral et al. | |
| 5,874,500 A | 2/1999 | Rhee et al. | |
| 6,051,648 A | 4/2000 | Rhee et al. | |
| 6,121,375 A | 9/2000 | Eknoian | |
| 6,150,472 A | 11/2000 | Engbers | |
| 6,165,488 A | 12/2000 | Tardy et al. | |
| 6,166,130 A | 12/2000 | Rhee et al. | |
| 6,323,278 B2 | 11/2001 | Rhee et al. | |
| 6,391,939 B2 | 5/2002 | Tayot et al. | |
| 6,410,519 B1 | 6/2002 | Gruskin et al. | |
| 6,458,147 B1 | 10/2002 | Cruise et al. | |
| 6,458,889 B1 | 10/2002 | Trollsas et al. | |
| 6,465,694 B1 | 10/2002 | Baudys et al. | |
| 6,514,534 B1 | 2/2003 | Sawhney | |
| 6,534,591 B2 | 3/2003 | Rhee et al. | |
| 6,602,952 B1 | 8/2003 | Bentley et al. | |
| 6,620,125 B1 | 9/2003 | Redl | |
| 6,696,089 B2 | 2/2004 | Kabanov et al. | |
| 6,703,047 B2 | 3/2004 | Sawhney et al. | |
| 6,756,518 B2 | 6/2004 | Gruskin et al. | |
| 6,800,278 B1 | 10/2004 | Perrault et al. | |
| 6,833,408 B2 | 12/2004 | Sehl et al. | |
| 6,858,736 B2 | 2/2005 | Nho et al. | |
| 7,217,845 B2 | 5/2007 | Rosen et al. | |
| 7,834,065 B2 | 11/2010 | Nakajima et al. | |
| 7,960,498 B2 | 6/2011 | Chenault et al. | |
| 2002/0151520 A1 | 10/2002 | Gruskin | |
| 2003/0022216 A1 | 1/2003 | Mao et al. | |
| 2003/0027788 A1 | 2/2003 | Singh et al. | |
| 2003/0064502 A1 | 4/2003 | Illman et al. | |
| 2003/0087111 A1 | 5/2003 | Hubbell et al. | |
| 2003/0108511 A1 | 6/2003 | Sawhney | |

(Continued)

FOREIGN PATENT DOCUMENTS

| | | |
|---|---|---|
| EP | 0961783 | 1/2007 |
| JP | 1982-102932 | 6/1982 |

(Continued)

OTHER PUBLICATIONS

Cortesi et al. Dextran Cross-Linked Gelatin Microspheres As a Drug Delivery System, European Journal of Pharmaceutics and Biopharmaceutics 47 (1999) 153-160.*

Thome, J., et al., "Ultrathin Antibacterial Polyammonium Coatings on Polymer Surfaces"; Surface and Coatings Technology, 174-175, 2003, pp. 584-587.

Harris, J. Milton, "Laboratory Synthesis of Polyethylene Glycol Derivatives", JMS—Rev., Macromol. Chem. Phys., C25 (3), 1985, pp. 325-373.

Harris, J. Milton, et al., "Synthesis of New Poly(Ethylene Glycol) Derivatives", PolyEthylene Glycol Chemistry: Biotechnical and Biomedical Applications, edited by Milton J. Harris, Plenum Press: New York, 1992, pp. 371-381.

Chen, Nicole, et al., "Mechanisms of Aldehyde-Containing Paper Wet-Strength Resins", Industrial & Engineering Chemistry Research, vol. 41, No. 22, 2002, pp. 5366-5371.

(Continued)

*Primary Examiner* — David J Blanchard
*Assistant Examiner* — Sarah Chickos
(74) *Attorney, Agent, or Firm* — McCarter & English

(57) ABSTRACT

A high swell, long-lived hydrogel sealant formed by reacting a highly oxidized polysaccharide containing aldehyde groups with a multi-arm amine is described. The hydrogel sealant may be particularly suitable for applications requiring high swell and slow degradation, for example, tissue augmentation, both cosmetic and reconstructive; void filling; tissue bulking, for example treatment of urinary incontinence and acid reflux; and embolization. The high swell, long-lived hydrogel sealant may also be useful as a tissue sealant and adhesive, and as an anti-adhesion barrier.

20 Claims, No Drawings

(56) References Cited

U.S. PATENT DOCUMENTS

| | | |
|---|---|---|
| 2003/0119985 A1 | 6/2003 | Sehl et al. |
| 2004/0086479 A1 | 5/2004 | Grinstaff et al. |
| 2004/0096507 A1 | 5/2004 | Kwang et al. |
| 2004/0225097 A1 | 11/2004 | Nho et al. |
| 2004/0235708 A1 | 11/2004 | Rhee et al. |
| 2005/0002893 A1 | 1/2005 | Goldmann |
| 2005/0020805 A1 | 1/2005 | Sunkara et al. |
| 2005/0288684 A1 | 12/2005 | Aronson et al. |
| 2006/0078536 A1 | 4/2006 | Kodokian et al. |
| 2006/0115531 A1 | 6/2006 | Chenault |
| 2006/0292030 A1 | 12/2006 | Odermatt et al. |
| 2007/0031467 A1 | 2/2007 | Abrahams et al. |
| 2007/0048251 A1 | 3/2007 | Arthur |
| 2007/0249870 A1 | 10/2007 | Chenault |
| 2008/0220047 A1 | 9/2008 | Sawhney et al. |
| 2008/0319101 A1 | 12/2008 | Nakajima et al. |
| 2009/0054535 A1 | 2/2009 | Figuly et al. |
| 2010/0086678 A1 | 4/2010 | Arthur et al. |
| 2010/0112063 A1 | 5/2010 | Figuly et al. |

FOREIGN PATENT DOCUMENTS

| | | |
|---|---|---|
| JP | 1988-11167 | 1/1988 |
| WO | WO 87/00836 | 2/1987 |
| WO | WO 90/10441 | 9/1990 |
| WO | WO 91/15368 | 10/1991 |
| WO | WO 97/30103 | 8/1997 |
| WO | WO 99/01143 | 1/1999 |
| WO | WO 00/69925 | 11/2000 |
| WO | WO 01/49268 | 7/2001 |
| WO | WO 01/72280 | 10/2001 |
| WO | WO 01/87986 | 11/2001 |
| WO | WO 02/102864 | 12/2002 |
| WO | WO 03/020818 | 3/2003 |
| WO | WO 03/097759 | 11/2003 |
| WO | WO 2006/031358 | 3/2006 |
| WO | WO 2006/042161 | 4/2006 |
| WO | WO 2006/080523 | 8/2006 |
| WO | WO 2006/086510 | 8/2006 |
| WO | WO 2008/005207 | 1/2008 |
| WO | WO 2008/066787 | 6/2008 |
| WO | WO 2009/064977 | 5/2009 |
| WO | WO/2009/064977 | 5/2009 |
| WO | WO 2010/059279 | 5/2010 |
| WO | WO 2010/059280 | 5/2010 |
| WO | WO 2010/111570 | 9/2010 |
| WO | WO 2010/118284 | 10/2010 |

OTHER PUBLICATIONS

Callant, Dominique, et al., "A New Approach to Dextran Derivatives with Pendent Aldehyde Groups", Reactive Polymers, vol. 8, 1988, pp. 129-136.
Hollander, Andreas, et al., "Polymer Surface Chemistry for Biologically Active Materials", Applied Surface Science, vol. 235, 2004, pp. 145-150.
Stone, H. Harlan, et al., "Antibiotic Prophylaxis in Gastric, Biliary and Colonic Surgery", Ann. Surg; Oct. 1976, pp. 443-450.
Fishman, Alexander, et al., "Synthesis and Investigation of Novel Branched PEG-Based Soluble Polymer Supports", The Journal of Organic Chemistry, vol. 68, 2003, pp. 9843-9846.
Newkome, George R., "Improved Synthesis of an Ethereal Tetraamine Core for Dendrimer Construction", The Journal of Organic Chemistry, vol. 67, 2002, pp. 3957-3960.
Halabi, A., et al., "Synthesis and Characterization of a Novel Dendritic Acrylic Monomer", The Journal of Organic Chemistry, vol. 65, 2000, pp. 9210-9213.
Harris, J. Milton, et al., "Synthesis and Characterization of Poly(ethylene Glycol) Derivatives", Journal of Polymer Science: Polymer Chemistry Edition, vol. 22, 1984, pp. 341-352.
Merrill, Edward W., "Poly(ethylene oxide) Star Molecules: Synthesis, Characterization, and Applications in Medicine and Biology", Journal of Biomaterials Science Polymer Edition, vol. 5, No. 1/2, 1993, pp. 1-11.
Zhao, Xuan, et al., "Novel Degradable Poly(ethylene glycol) Esters for Drug Delivery", Poly(ethylene glycol) Chemistry and Biological Applications, Oxford University Press, 1998, Chapter 28, pp. 458-472.
Azzam, Tony, et al., "Cationic Polysaccharides for Gene Delivery", Macromolecules, vol. 35, No. 27, 2002, pp. 9947-9953.
Nagasaki, Yukio, et al., "Formyl-Ended Heterobifunctional Poly(ethylene oxide): Synthesis of Poly(ethylene oxide) with a Formyl Group at One End and a Hydroxyl Group at the Other End", Bioconjugate Chemistry, vol. 6, No. 2, 1995, pp. 231-233.
Greenwald, Richard B., et al., "Drug Delivery Systems Employing 1,4- or 1,6-Elimination: Poly(ethylene glycol) Prodrugs of Amine-Containing Compounds", Journal of Medicinal Chemistry, vol. 42, No. 18, 1999, pp. 3657-3667.
Zalipsky, Samuel, et al., "Preparation and Applications of Polyethylene Glycol—Polystyrene Graft Resin Supports for Solid-Phase Peptide Synthesis", Reactive Polymers, vol. 22, 1994, pp. 243-258.
Lara, V.S., et al., "Dentin-Induced In Vivo Inflammatory Response and In Vitro Activation of Murine Macrophages", Journal of Dental Research, vol. 82, No. 6, 2003, pp. 460-465.
Atassi, M.Z., "Immunochemistry of Proteins", vol. 1, Plenum Press, New York, 1977, pp. 59-60.
Sweeney, Thomas, et al., "Intestinal Anastomoses Detected with a Photopolymerized Hydrogel", Surgery, vol. 131, No. 2, Feb. 2002, pp. 185-189.
Kim, Jae Chan, et al., "Evaluation of Tissue Adhesives in Closure of Scleral Tunnel Incisions", Journal of Cataract & Refractive Surgery, vol. 21, May 1995, pp. 320-325.
Sarayba, Melvin A., et al., "Inflow of Ocular Surface Fluid Through Clear Corneal Cataract Incisions: A Laboratory Model", American Journal of Ophthalmology, vol. 138, No. 2, Aug. 2004, pp. 206-210.
Buckmann, Andreas F., et al., "Functionalization of Poly(ethylene glycol) and Monomethoxy-Poly(ethylene glycol)", Makromolecular Chemistry, vol. 182, 1981, pp. 1379-1384.
Bruce, J., et al., "Systematic Review of the Definition and Measurement of Anastomotic Leak after Gastrointestinal Surgery", British Journal of Surgery, vol. 88, 2001, pp. 1157-1168.
Mo, Xiumei, et al,, "Soft Tissue Adhesive Composed of Modified Gelatin and Polysaccharides", Journal of Biomaterials Science Polymer Edition, vol. 11, No. 4, 2000, pp. 341-351.
Hofreiter, B.T., et al., "Rapid Estimation of Dialdehyde Content of Periodate Oxystarch through Quantitative Alkali Consumption", Analytical Chemistry, vol. 27, No. 12, Dec. 1955, pp. 1930-1931.
Zhao, Huiru, et al., "Determination of Degree of Substitution of Formyl Groups in Polyaldehyde Dextran by the Hydroxylamine Hydrochloride Method", Pharmaceutical Research, vol. 8, No. 3, 1991, pp. 400-402.
Kurisawa, Motoichi, et al., "Double-Stimuli-Responsive Degradation of Hydrogels Consisting of Oligopeptide-Terminated Poly(ethylene glycol) and Dextran with an Interpenetrating Polymer Network", Journal of Biomaterials Science Polymer Edition, vol. 8, No. 9, 1997, pp. 691-708.
Pfannemuller, B., et al., "Chemical Modification of the Surface of the Starch Granules", Starch/Starke, vol. 95, No. 9, 1983, pp. 298-303.
Specification of U.S. Appl. No. 13/102,262.

\* cited by examiner

HIGH SWELL, LONG-LIVED HYDROGEL SEALANT

CROSS-REFERENCE TO RELATED APPLICATION

This application claims priority under 35 U.S.C. §119 from U.S. Provisional Application Ser. No. 61/135,173, filed Jul. 17, 2008.

FIELD OF THE INVENTION

The invention relates to the field of medical adhesives. More specifically, the invention relates to a high swell, long-lived hydrogel sealant formed by reacting a highly oxidized polysaccharide containing aldehyde groups with a multi-arm amine.

BACKGROUND OF THE INVENTION

Tissue adhesives have many potential medical applications, including wound closure, supplementing or replacing sutures or staples in internal surgical procedures, adhesion of synthetic onlays or inlays to the cornea, drug delivery devices, and as anti-adhesion barriers to prevent post-surgical adhesions. Conventional tissue adhesives are generally not suitable for a wide range of adhesive applications. For example, cyanoacrylate-based adhesives have been used for topical wound closure, but the release of toxic degradation products limits their use for internal applications. Fibrin-based adhesives are slow curing, have poor mechanical strength, and pose a risk of viral infection. Additionally, the fibrin-based adhesives do not bond covalently to the underlying tissue.

Several types of hydrogel tissue adhesives have been developed, which have improved adhesive and cohesive properties and are nontoxic. These hydrogels are generally formed by reacting a component having nucleophilic groups with a component having electrophilic groups, which are capable of reacting with the nucleophilic groups of the first component, to form a crosslinked network via covalent bonding. However, these hydrogels typically swell or dissolve away too quickly, or lack sufficient adhesion or mechanical strength, thereby decreasing their effectiveness as surgical adhesives.

Kodokian et al. (copending and commonly owned U.S. Patent Application Publication No. 2006/0078536) describe hydrogel tissue adhesives formed by reacting an oxidized polysaccharide with a water-dispersible, multi-arm polyether amine. These adhesives provide improved adhesion and cohesion properties, crosslink readily at body temperature, maintain dimensional stability initially, do not degrade rapidly, and are nontoxic to cells and non-inflammatory to tissue. However, for certain applications, including but not limited to, tissue augmentation, both cosmetic and reconstructive; void filling; tissue bulking, for example treatment of urinary incontinence and acid reflux; and embolization, hydrogel sealants with high swell and slow degradation are needed.

Therefore, the problem to be solved is to provide a hydrogel material having high swell and a slow degradation rate for use in certain surgical procedures and other medical applications that require these properties.

SUMMARY OF THE INVENTION

The stated problem is addressed herein by the discovery that a high swell, long-lived hydrogel sealant is formed by reacting at least one highly oxidized polysaccharide containing aldehyde groups with at least one water-dispersible, multi-arm amine at the conditions described herein. Methods of using the low swell, long-lived hydrogel sealant for medical purposes are also provided.

Accordingly, in one aspect the present invention provides a kit comprising:
a) a first aqueous solution or dispersion comprising at least one highly oxidized polysaccharide containing aldehyde groups, said highly oxidized polysaccharide having a weight-average molecular weight of about 1,000 to about 1,000,000 Daltons and an equivalent weight per aldehyde group of about 65 to about 85 Daltons, wherein said first aqueous solution or dispersion contains said highly oxidized polysaccharide at a concentration of greater than or equal to about 3% but less than 6% by weight; and
b) a second aqueous solution or dispersion comprising at least one water-dispersible, multi-arm amine wherein at least three of the arms are terminated by at least one primary amine group, said multi-arm amine having a number-average molecular weight of about 450 to about 200,000 Daltons, wherein said second aqueous solution or dispersion contains said multi-arm amine at a concentration of about 5% to about 70% by weight;
provided that:
(i) if the concentration of the highly oxidized polysaccharide in the first aqueous solution or dispersion is equal to or greater than 5 wt % but less than 6 wt %, the equivalent weight per aldehyde group of the highly oxidized polysaccharide is about 80 to about 85 Daltons;
(ii) if the concentration of the highly oxidized polysaccharide in the first aqueous solution or dispersion is equal to or greater than 3 wt % but less than 5 wt %, the equivalent weight per aldehyde group of the highly oxidized polysaccharide is about 65 to about 85 Daltons.

In another aspect, the present invention provides a dried hydrogel formed by a process comprising the steps of:
a) combining (i) a first solution or dispersion comprising at least one highly oxidized polysaccharide containing aldehyde groups in a first solvent, said oxidized polysaccharide having a weight-average molecular weight of about 1,000 to about 1,000,000 Daltons and an equivalent weight per aldehyde group of about 65 to about 85 Daltons, said first solution or dispersion containing said highly oxidized polysaccharide at a concentration of greater than or equal to about 3% but less than 6% by weight; with (ii) a second solution or dispersion comprising at least one water-dispersible, multi-arm amine in a second solvent, wherein at least three of the arms of the multi-arm amine are terminated by at least one primary amine group, said multi-arm amine having a number-average molecular weight of about 450 to about 200,000 Daltons, wherein said second solution or dispersion contains said multi-arm amine at a concentration of about 5% to about 70% by weight, to form a hydrogel, wherein the first solvent is either the same as or different from the second solvent; and
b) treating the hydrogel to remove at least a portion of said first solvent and said second solvent to form the dried hydrogel;
provided that:
(i) if the concentration of the highly oxidized polysaccharide in the first solution or dispersion is equal to or greater than 5 wt % but less than 6 wt %, the equivalent weight per aldehyde group of the highly oxidized polysaccharide is about 80 to about 85 Daltons;
(ii) if the concentration of the highly oxidized polysaccharide in the first solution or dispersion is equal to or greater than 3 wt % but less than 5 wt %, the equivalent weight per aldehyde group of the highly oxidized polysaccharide is about 65 to about 85 Daltons.

In another aspect, the present invention provides a method for applying a coating to an anatomical site on tissue of a living organism comprising: applying to the site (a) a first aqueous solution or dispersion comprising at least one highly oxidized polysaccharide containing aldehyde groups, said highly oxidized polysaccharide having a weight-average molecular weight of about 1,000 to about 1,000,000 Daltons and an equivalent weight per aldehyde group of about 65 to about 85 Daltons, wherein said first aqueous solution or dispersion contains said highly oxidized polysaccharide at a concentration of greater than or equal to about 3% but less than 6% by weight; followed by (b) a second aqueous solution or dispersion comprising at least one water-dispersible, multi-arm amine wherein at least three of the arms are terminated by at least one primary amine group, said multi-arm amine having a number-average molecular weight of about 450 to about 200,000 Daltons, wherein said second aqueous solution or dispersion contains said multi-arm amine at a concentration of about 5% to about 70% by weight, or
applying (b) followed by (a) and mixing (a) and (b) on the site, or
premixing (a) and (b) to form a mixture and applying said mixture to the site;
provided that:
(i) if the concentration of the highly oxidized polysaccharide in the first aqueous solution or dispersion is equal to or greater than 5 wt % but less than 6 wt %, the equivalent weight per aldehyde group of the highly oxidized polysaccharide is about 80 to about 85 Daltons;
(ii) if the concentration of the highly oxidized polysaccharide in the first aqueous solution or dispersion is equal to or greater than 3 wt % but less than 5 wt %, the equivalent weight per aldehyde group of the highly oxidized polysaccharide is about 65 to about 85 Daltons.

In another aspect, the present invention provides a method for bonding at least two anatomical sites together comprising: applying to at least one site (a) a first aqueous solution or dispersion comprising at least one highly oxidized polysaccharide containing aldehyde groups, said highly oxidized polysaccharide having a weight-average molecular weight of about 1,000 to about 1,000,000 Daltons and an equivalent weight per aldehyde group of about 65 to about 85 Daltons, wherein said first aqueous solution or dispersion contains said highly oxidized polysaccharide at a concentration of greater than or equal to about 3% but less than 6% by weight; applying to at least one of either the same site or one other site (b) a second aqueous solution or dispersion comprising at least one water-dispersible, multi-arm amine wherein at least three of the arms are terminated by at least one primary amine group, said multi-arm amine having a number-average molecular weight of about 450 to about 200,000 Daltons, wherein said second aqueous solution or dispersion contains said multi-arm amine at a concentration of about 5% to about 70% by weight; or premixing (a) and (b) to form a mixture and applying said mixture to at least one site before the mixture completely cures; and contacting the at least two anatomical sites together;
provided that:
(i) if the concentration of the highly oxidized polysaccharide in the first aqueous solution or dispersion is equal to or greater than 5 wt % but less than 6 wt %, the equivalent weight per aldehyde group of the highly oxidized polysaccharide is about 80 to about 85 Daltons;
(ii) if the concentration of the highly oxidized polysaccharide in the first aqueous solution or dispersion is equal to or greater than 3 wt % but less than 5 wt %, the equivalent weight per aldehyde group of the highly oxidized polysaccharide is about 65 to about 85 Daltons.

In another embodiment, the invention provides a method for completely or partially blocking or filling a lumen or void within the body of humans or animals comprising the steps of: applying into said lumen or void (a) a first aqueous solution or dispersion comprising at least one highly oxidized polysaccharide containing aldehyde groups, said highly oxidized polysaccharide having a weight-average molecular weight of about 1,000 to about 1,000,000 Daltons and an equivalent weight per aldehyde group of about 65 to about 85 Daltons, wherein said first aqueous solution or dispersion contains said highly oxidized polysaccharide at a concentration of greater than or equal to about 3% but less than 6% by weight; followed by (b) a second aqueous solution or dispersion comprising at least one water-dispersible, multi-arm amine wherein at least three of the arms are terminated by at least one primary amine group, said multi-arm amine having a number-average molecular weight of about 450 to about 200,000 Daltons, wherein said second aqueous solution or dispersion contains said multi-arm amine at a concentration of about 5% to about 70% by weight, or
applying (b) followed by (a), or applying (a) and (b) simultaneously or
premixing (a) and (b) to form a mixture and applying said mixture to the lumen or void;
provided that:
(i) if the concentration of the highly oxidized polysaccharide in the first aqueous solution or dispersion is equal to or greater than 5 wt % but less than 6 wt %, the equivalent weight per aldehyde group of the highly oxidized polysaccharide is about 80 to about 85 Daltons;
(ii) if the concentration of the highly oxidized polysaccharide in the first aqueous solution or dispersion is equal to or greater than 3 wt % but less than 5 wt %, the equivalent weight per aldehyde group of the highly oxidized polysaccharide is about 65 to about 85 Daltons.

In another embodiment, the invention provides a composition comprising the reaction product of:
a) a first aqueous solution or dispersion comprising at least one highly oxidized polysaccharide containing aldehyde groups, said highly oxidized polysaccharide having a weight-average molecular weight of about 1,000 to about 1,000,000 Daltons and an equivalent weight per aldehyde group of about 65 to about 85 Daltons, wherein said first aqueous solution or dispersion contains said highly oxidized polysaccharide at a concentration of greater than or equal to about 3% but less than 6% by weight; and
b) a second aqueous solution or dispersion comprising at least one water-dispersible, multi-arm amine wherein at least three of the arms are terminated by at least one primary amine group, said multi-arm amine having a number-average molecular weight of about 450 to about 200,000 Daltons, wherein said second aqueous solution or dispersion contains said multi-arm amine at a concentration of about 5% to about 70% by weight;
provided that:
(i) if the concentration of the highly oxidized polysaccharide in the first aqueous solution or dispersion is equal to or greater than 5 wt % but less than 6 wt %, the equivalent weight per aldehyde group of the highly oxidized polysaccharide is about 80 to about 85 Daltons;

(ii) if the concentration of the highly oxidized polysaccharide in the first aqueous solution or dispersion is equal to or greater than 3 wt % but less than 5 wt %, the equivalent weight per aldehyde group of the highly oxidized polysaccharide is about 65 to about 85 Daltons.

DETAILED DESCRIPTION OF THE INVENTION

Disclosed herein is a high swell, long-lived hydrogel sealant formed by reacting at least one highly oxidized polysaccharide containing aldehyde groups, having an equivalent weight per aldehyde group of about 65 to about 85 Daltons, with at least one water-dispersible multi-arm amine at the conditions disclosed herein. The high swell, long-lived hydrogel sealant may be particularly useful in medical applications where high swell and slow degradation are needed, including but not limited to, tissue augmentation, both cosmetic and reconstructive; void filling; tissue bulking, for example treatment of urinary incontinence and acid reflux; and embolization. The high swell, long-lived hydrogel sealant may also be useful as a tissue sealant and adhesive, and as an anti-adhesion barrier.

The following definitions are used herein and should be referred to for interpretation of the claims and the specification.

The term "oxidized polysaccharide" refers to a polysaccharide that has been reacted with an oxidizing agent to introduce aldehyde groups into the molecule.

The term "highly oxidized polysaccharide" as used herein, refers to an oxidized polysaccharide that has an equivalent weight per aldehyde group of about 65 to about 85 Daltons.

The term "equivalent weight per aldehyde group" refers to the average molecular weight of the compound divided by the number of aldehyde groups in the molecule.

The term "water-dispersible, multi-arm amine" refers to a polymer having three or more polymer chains ("arms"), which may be linear or branched, emanating from a central structure, which may be a single atom, a core molecule, or a polymer backbone, wherein at least three of the branches ("arms") are terminated by at least one primary amine group. The water-dispersible, multi-arm amine is water soluble or is able to be dispersed in water to form a colloidal suspension capable of reacting with a second reactant in aqueous solution or dispersion.

The term "dispersion" as used herein, refers to a colloidal suspension capable of reacting with a second reactant in an aqueous medium.

The term "water-dispersible, multi-arm polyether amine" refers to a water-dispersible, multi-arm amine wherein the polymer is a polyether.

The term "polyether" refers to a polymer having the repeat unit [—O—R]—, wherein R is a hydrocarbylene group having 2 to 5 carbon atoms. The polyether may also be a random or block copolymer comprising different repeat units which contain different R groups.

The term "hydrocarbylene group" refers to a divalent group formed by removing two hydrogen atoms, one from each of two different carbon atoms, from a hydrocarbon.

The term "branched polyether" refers to a polyether having one or more branch points ("arms"), including star, dendritic, comb, highly branched, and hyperbranched polyethers.

The term "dendritic polyether" refers to a highly branched polyether having a branching structure that repeats regularly with each successive generation of monomer, radiating from a core molecule.

The term "comb polyether" refers to a multi-arm polyether in which linear side chains emanate from trifunctional branch points on a linear polymer backbone.

The term "star polyether" refers to a multi-arm polyether in which linear side chains emanate from a single atom or a core molecule having a point of symmetry.

The term "highly branched polyether" refers to a multi-arm polyether having many branch points, such that the distance between branch points is small relative to the total length of the arms.

The term "hyperbranched polyether" refers to a multi-arm polyether that is more branched than highly branched with order approaching that of an imperfect dendritic polyether.

The term "branched end amine" refers to a linear or multi-arm polymer having two or three primary amine groups at each of the ends of the polymer chain or at the end of the polymer arms.

The term "multi-functional amine" refers to a chemical compound comprising at least two functional groups, at least one of which is a primary amine group.

The term "hydrogel" refers to a water-swellable polymeric matrix, consisting of a three-dimensional network of macromolecules held together by covalent or non-covalent crosslinks, that can absorb a substantial amount of water to form an elastic gel.

The term "high swell, long-lived hydrogel" as used herein, refers to a hydrogel formed by reacting a highly oxidized polysaccharide having an equivalent weight per aldehyde group of about 65 to about 85 Daltons and a multi-arm amine at the conditions described herein. The high swell, long-lived hydrogel has a higher maximum swell and a slower degradation than a hydrogel formed from the same oxidized polysaccharide having an equivalent weight per aldehyde group of greater than or equal to about 90 Daltons and the same multi-arm amine at the same total solids content.

The term "maximum swell" as used herein, refers to the maximum weight that a hydrogel attains when soaked in an aqueous solution, such as phosphate buffered saline (PBS), for a period of time, divided by the initial weight of the hydrogel, multiplied by 100.

The term "dried hydrogel" refers to a hydrogel that has been treated to remove at least a portion of the solvent(s) contained therein. Preferably, substantially all of the solvent(s) is/are removed from the hydrogel.

The term "% by weight", also referred to herein as "wt %", refers to the weight percent relative to the total weight of the solution or dispersion, unless otherwise specified.

The term "anatomical site" refers to any external or internal part of the body of humans or animals.

The term "tissue" refers to any tissue, both living and dead, in humans or animals.

By medical application is meant medical applications as related to humans and animals.

The term "lumen" refers to any hollow organ or vessel of the body, including but not limited to, Fallopian tubes, veins, arteries, intestines, trachea, and the like.

The term "void" refers to any hollow space created by congenital abnormalities, disease, aging, or surgery, including but not limited to, lesions, fissures, fistulae, cysts, diverticulae, aneurysms, and any other undesirable void present in any tissue or organ of the body which may result from congenital abnormalities, disease, aging, or surgery.

Highly Oxidized Polysaccharides

The polysaccharides useful in the invention are oxidized to contain aldehyde groups. Suitable starting polysaccharides include, but are not limited to, dextran, starch, agar, cellulose, and hyaluronic acid. These polysaccharides are available commercially from sources such as Sigma-Aldrich (Milwaukee, Wis.) and Pharmacosmos A/S (Holbaek, Denmark). Typically, commercial preparations of polysaccharides are a heterogeneous mixture having a distribution of different molecular weights and are characterized by various molecular weight averages, for example, the weight-average molecular weight, or the number-average molecular weight, as is known in the art. Suitable polysaccharides have a weight-average molecular weight of about 1,000 to about 1,000,000 Daltons, more particularly from about 3,000 to about 500,000 Daltons.

The polysaccharides may be oxidized to contain aldehyde groups using methods known in the art. Highly oxidized polysaccharides may be prepared by oxidation of polysaccharides using any suitable oxidizing agent, including but not limited to, periodates, hypochlorites, ozone, peroxides, hydroperoxides, persulfates, and percarbonates. In one embodiment, the polysaccharide is oxidized by reaction with sodium periodate, for example as described by Mo et al. (*J. Biomater. Sci. Polymer Edn.* 11:341-351, 2000). Additionally, the highly oxidized polysaccharide may be prepared using the method described by Cohen et al. (copending and commonly owned Patent Application No. PCT/US08/05013 (WO 2008/133847)). That method of making an oxidized polysaccharide comprises a combination of precipitation and separation steps to purify the oxidized polysaccharide formed by oxidation of the polysaccharide with periodate and provides an oxidized polysaccharide with very low levels of iodine-containing species. The polysaccharide may be reacted with different amounts of periodate to give polysaccharides with different degrees of oxidation and therefore, different amounts of aldehyde groups, as described in detail in the General Methods section of the Examples herein. Specifically, the amount of oxidizing agent is chosen to provide a highly oxidized polysaccharide having an equivalent weight per aldehyde group of about 65 to about 85 Daltons.

The aldehyde content of the highly oxidized polysaccharide may be determined using methods known in the art. For example, the dialdehyde content of the highly oxidized polysaccharide, also referred to herein as the oxidation conversion, may be determined using the method described by Hofreiter et al. (*Anal Chem.* 27:1930-1931, 1955). In that method, the amount of alkali consumed per mole of dialdehyde in the highly oxidized polysaccharide, under specific reaction conditions, is determined by a pH titration. Alternatively, the oxidation conversion of the highly oxidized polysaccharide may be determined using nuclear magnetic resonance (NMR) spectroscopy, as described in the Examples herein.

Suitable highly oxidized polysaccharides containing aldehyde groups have a weight-average molecular weight of about 1,000 to about 1,000,000 Daltons, more particularly from about 3,000 to about 500,000 Daltons; and an equivalent weight per aldehyde group of about 65 to about 85 Daltons. In another embodiment, the equivalent weight per aldehyde group of the highly oxidized polysaccharide is about 70 to about 80 Daltons. In another embodiment, the equivalent weight per aldehyde group of the highly oxidized polysaccharide is about 80 to about 85 Daltons.

In one embodiment, the highly oxidized polysaccharide containing aldehyde groups is oxidized dextran having a weight-average molecular weight of about 8,500 to about 11,500 Daltons and an equivalent weight per aldehyde group of about 73 Daltons (oxidation conversion of about 91%).

In another embodiment, the highly oxidized polysaccharide containing aldehyde groups is oxidized dextran having a weight-average molecular weight of about 8,500 to about 11,500 Daltons and an equivalent weight per aldehyde group of about 80 Daltons (oxidation conversion of about 84%).

In another embodiment, the highly oxidized polysaccharide containing aldehyde groups is oxidized dextran having a weight-average molecular weight of about 60,000 to about 90,000 Daltons and an equivalent weight per aldehyde group of about 71 Daltons (oxidation conversion of about 93%).

In another embodiment, the highly oxidized polysaccharide containing aldehyde groups is oxidized dextran having a weight-average molecular weight of about 60,000 to about 90,000 Daltons and an equivalent weight per aldehyde group of about 77 Daltons (oxidation conversion of about 87%).

In another embodiment, the highly oxidized polysaccharide containing aldehyde groups is oxidized dextran having a weight-average molecular weight of about 400,000 to about 500,000 Daltons and an equivalent weight per aldehyde group of about 77 Daltons (oxidation conversion of about 87%).

Water-Dispersible, Multi-Arm Amines

Suitable water dispersible, multi-arm amines include, but are not limited to, water dispersible multi-arm polyether amines, amino-terminated dendritic polyamidoamines, and multi-arm branched end amines. Typically, the multi-arm amines have a number-average molecular weight of about 450 to about 200,000 Daltons, more particularly from about 2,000 to about 40,000 Daltons.

In one embodiment, the water dispersible, multi-arm amine is a multi-arm polyether amine, which is a water-dispersible polyether having the repeat unit [—O—R]—, wherein R is a hydrocarbylene group having 2 to 5 carbon atoms. Suitable multi-arm polyether amines include, but are not limited to, dendritic, comb, star, highly branched, and hyperbranched polyethers wherein at least three of the arms are terminated by at least one primary amine group. Examples of water-dispersible, multi-arm polyether amines include, but are not limited to, amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star polyethylene oxide-polypropylene oxide copolymers, amino-terminated dendritic polyethylene oxide-polypropylene oxide copolymers, amino-terminated comb polyethylene oxide-polypropylene oxide copolymers, and polyoxyalkylene triamines sold under the trade name JEFFAMINE® triamines, by Huntsman LLC. (Houston, Tex.). Examples of star polyethylene oxide amines, include, but are not limited to, various multi-arm polyethylene glycol amines, available for example from Nektar Transforming Therapeutics (Huntsville, Ala.), and star polyethylene glycols having 3, 4, 6, or 8 arms terminated with primary amines (referred to herein as 3, 4, 6 or 8-arm star PEG amines, respectively). The 8-arm star PEG amine is available from Nektar Transforming Therapeutics. Examples of suitable JEFFAMINE® triamines include, but are not limited to, JEFFAMINE® T-403 (CAS No. 39423-51-3), JEFFAMINE® T-3000 (CAS No. 64852-22-8), and JEFFAMINE® T-5000 (CAS No. 64852-22-8).

In one embodiment, the water-dispersible multi-arm amine is an eight-arm polyethylene glycol having eight arms terminated by a primary amine group and having a number-average molecular weight of about 10,000 Daltons.

The multi-arm polyether amines are either available commercially, as noted above, or may be prepared using methods known in the art. For example, multi-arm polyethylene glycols, wherein at least three of the arms are terminated by a primary amine group, may be prepared by putting amine ends on multi-arm polyethylene glycols (e.g., 3, 4, 6, and 8-arm star polyethylene glycols, available from companies such as Nektar Transforming Therapeutics; SunBio, Inc., Anyang City, South Korea; NOF Corp., Tokyo, Japan; or JenKem Technology USA, Allen, Tex.) using the method described by Buckmann et al. (*Makromol. Chem.* 182:1379-1384, 1981). In that method, the multi-arm polyethylene glycol is reacted with thionyl bromide to convert the hydroxyl groups to bromines, which are then converted to amines by reaction with ammonia at 100° C. The method is broadly applicable to the preparation of other multi-arm polyether amines. Additionally, multi-arm polyether amines may be prepared from multi-arm polyols using the method described by Chenault (copending and commonly owned U.S. Patent Application Publication No. 2007/0249870). In that method, the multi-arm polyether is reacted with thionyl chloride to convert the hydroxyl groups to chlorine groups, which are then converted to amines by reaction with aqueous or anhydrous ammonia. Other methods that may used for preparing multi-arm polyether amines are described by Merrill et al. in U.S. Pat. No. 5,830,986, and by Chang et al. in WO 97/30103.

The multi-arm amine may also be an amino-terminated dendritic polyamidoamine, sold under the trade name Starburst® Dendrimers (available from Sigma-Aldrich, St Louis, Mo.).

The multi-arm amine may also be a multi-arm branched end amine, as described by Arthur (copending and commonly owned Patent Application No. PCT/US07/24393 (WO 2008/066787)). The multi-arm branched end amines are branched polymers having two or three primary amine groups at the end of each of the polymer arms. The multiplicity of functional groups increases the statistical probability of reaction at a given chain end and allows more efficient incorporation of the molecules into a polymer network. The starting materials used to prepare the multi-arm branched end amines are branched polymers such as multi-arm polyether polyols including, but not limited to, comb and star polyether polyols. The branched end amines can be prepared by attaching multiple amine groups to the end of the polymer arms using methods well known in the art. For example, a multi-arm branched end amine having two primary amine functional groups on the end of each of the polymer arms can prepared by reacting the starting material, as listed above, with thionyl chloride in a suitable solvent such as toluene to give the chloride derivative, which is subsequently reacted with tris (2-aminoethyl)amine to give the multi-arm branched end reactant having two amine groups at the end of the polymer arms.

It should be recognized that the multi-arm amines are generally a somewhat heterogeneous mixture having a distribution of arm lengths and in some cases, a distribution of species with different numbers of arms. When a multi-arm amine has a distribution of species having different numbers of arms, it can be referred to based on the average number of arms in the distribution. For example, in one embodiment the multi-arm amine is an 8-arm star PEG amine, which comprises a mixture of multi-arm star PEG amines, some having less than and some having more than 8 arms; however, the multi-arm star PEG amines in the mixture have an average of 8 arms. Therefore, the terms "8-arm", "6-arm", "4-arm" and "3-arm" as used herein to refer to multi-arm amines, should be construed as referring to a heterogeneous mixture having a distribution of arm lengths and in some cases, a distribution of species with different numbers of arms, in which case the number of arms recited refers to the average number of arms in the mixture.

In one embodiment, the polysaccharide that is highly oxidized to contain aldehyde groups is dextran and the multi-arm amine is a multi-arm polyethylene glycol amine.

Methods of Using the High Swell, Long-Lived Hydrogel Sealant

The high swell, long-lived hydrogel sealant disclosed herein may be used in various forms. In one embodiment, the highly oxidized polysaccharide containing aldehyde groups and the multi-arm amine are used in the form of aqueous solutions or dispersions. To prepare an aqueous solution or dispersion comprising at least one highly oxidized polysaccharide (referred to herein as the "first aqueous solution or dispersion"), at least one highly oxidized polysaccharide, as described above, is added to water to give a concentration of greater than or equal to about 3% but less than 6% by weight relative to the total weight of the solution or dispersion. Mixtures of different highly oxidized polysaccharides, having different average molecular weights and/or different equivalent weights per aldehyde group may also be used. If a mixture of different highly oxidized polysaccharides is used, the total concentration of the polysaccharides is greater than or equal to about 3% but less than 6% by weight relative to the total weight of the solution or dispersion. In one embodiment, the concentration of the highly oxidized polysaccharide in the first aqueous solution or dispersion is about 4% by weight relative to the total weight of the solution or dispersion.

The degree of swell of the high swell, long-lived hydrogel disclosed herein is governed by its crosslink density, which depends on several factors including the concentration of the highly oxidized polysaccharide in the first aqueous solution or dispersion and the equivalent weight per aldehyde group of the highly oxidized polysaccharide. Therefore, where the concentration of the highly oxidized polysaccharide in the first aqueous solution or dispersion is equal to or greater than 5 wt % but less than 6 wt %, the equivalent weight per aldehyde group of the highly oxidized polysaccharide is about 80 to about 85 Daltons in order to obtain a crosslink density that results in a hydrogel with high swell. Where the concentration of the highly oxidized polysaccharide in the first aqueous solution or dispersion is equal to or greater than 3 wt % but less than 5 wt %, the equivalent weight per aldehyde group of the highly oxidized polysaccharide is about 65 to about 85 Daltons.

To prepare an aqueous solution or dispersion comprising at least one water-dispersible multi-arm amine (referred to herein as the "second aqueous solution or dispersion"), at least one multi-arm amine is added to water to give a concentration of about of 5% to about 70% by weight, more particularly about 15% to about 50% by weight, more particularly about 30% to about 50% by weight, relative to the total weight of the solution or dispersion. Mixtures of different multi-arm amines may also be used. If a mixture of different multi-arm amines is used, the total concentration of the multi-arm amines is about 5% to about 70% by weight, more particularly about 15% to about 50% by weight, more particularly about 30% to about 50% by weight, relative to the total weight of the solution or dispersion. The optimal concentrations of the two aqueous solutions or dispersions to be used depend on the application, and can be readily determined by one skilled in the art using routine experimentation.

For use on living tissue, it is preferred that the first aqueous solution or dispersion and the second aqueous solution or dispersion be sterilized to prevent infection. Any suitable sterilization method known in the art that does not adversely affect the ability of the components to react to form an effective hydrogel may be used, including, but not limited to, electron beam irradiation, gamma irradiation, ethylene oxide sterilization, or ultra-filtration through a 0.2 μm pore membrane.

The first aqueous solution or dispersion and/or the second aqueous solution or dispersion may further comprise various additives depending on the intended application. Preferably, the additive is compatible with the other components of the solution. Specifically, the additive does not contain groups that would interfere with effective gelation of the hydrogel. The amount of the additive used depends on the particular application and may be readily determined by one skilled in the art using routine experimentation. For example, the solution(s) or dispersion(s) may comprise at least one additive selected from the group consisting of pH modifiers, viscosity modifiers, colorants, surfactants, pharmaceutical drugs and therapeutic agents.

The solution(s) or dispersion(s) may optionally include at least one pH modifier to adjust the pH of the solution(s). Suitable pH modifiers are well known in the art. The pH modifier may be an acidic or basic compound. Examples of acidic pH modifiers include, but are not limited to, carboxylic acids, inorganic acids, and sulfonic acids. Examples of basic pH modifiers include, but are not limited to, hydroxides, alkoxides, nitrogen-containing compounds other than primary and secondary amines, and basic carbonates and phosphates.

The aqueous solution(s) or dispersion(s) may optionally include at least one thickener. The thickener may be selected from among known viscosity modifiers, including, but not limited to, polysaccharides and derivatives thereof, such as starch or hydroxyethyl cellulose.

The aqueous solution(s) or dispersion(s) may optionally include at least one antimicrobial agent. Suitable antimicrobial preservatives are well known in the art. Examples of suitable antimicrobials include, but are not limited to, alkyl parabens, such as methylparaben, ethylparaben, propylparaben, and butylparaben; triclosan; chlorhexidine; cresol; chlorocresol; hydroquinone; sodium benzoate; and potassium benzoate.

The aqueous solution(s) or dispersion(s) may also optionally include at least one colorant to enhance the visibility of the solution(s). Suitable colorants include dyes, pigments, and natural coloring agents. Examples of suitable colorants include, but are not limited to, FD&C and D&C colorants, such as FD&C Violet No. 2, FD&C Blue No. 1, D&C Green No. 6, D&C Green No. 5, D&C Violet No. 2; and natural colorants such as beetroot red, canthaxanthin, chlorophyll, eosin, saffron, and carmine.

The aqueous solution(s) or dispersion(s) may also optionally include at least one surfactant. Surfactant, as used herein, refers to a compound that lowers the surface tension of water. The surfactant may be an ionic surfactant, such as sodium lauryl sulfate, or a neutral surfactant, such as polyoxyethylene ethers, polyoxyethylene esters, and polyoxyethylene sorbitan.

Additionally, the aqueous solution(s) or dispersion(s) may optionally include at least one pharmaceutical drug or therapeutic agent. Suitable drugs and therapeutic agents are well known in the art (for example see the United States Pharmacopeia (USP), *Physician's Desk Reference* (Thomson Publishing), *The Merck Manual of Diagnosis and Therapy* 18th ed., Mark H. Beers and Robert Berkow (eds.), Merck Publishing Group, 2006; or, in the case of animals, *The Merck Veterinary Manual,* 9th ed., Kahn, C. A. (ed.), Merck Publishing Group, 2005). Nonlimiting examples include, but are not limited to, anti-inflammatory agents, for example, glucocorticoids such as prednisone, dexamethasone, budesonide; non-steroidal anti-inflammatory agents such as indomethacin, salicylic acid acetate, ibuprofen, sulindac, piroxicam, and naproxen; fibrinolytic agents such as a tissue plasminogen activator and streptokinase; anti-coagulants such as heparin, hirudin, ancrod, dicumarol, sincumar, iloprost, L-arginine, dipyramidole and other platelet function inhibitors; antibodies; nucleic acids; peptides; hormones; growth factors; cytokines; chemokines; clotting factors; endogenous clotting inhibitors; antibacterial agents; antiviral agents; antifungal agents; anti-cancer agents; cell adhesion inhibitors; healing promoters; vaccines; thrombogenic agents, such as thrombin, fibrinogen, homocysteine, and estramustine; radio-opaque compounds, such as barium sulfate and gold particles and radiolabels.

Additionally, the second aqueous solution or dispersion comprising the multi-arm amine may optionally comprise at least one other multi-functional amine having one or more primary amine groups to provide other beneficial properties, such as hydrophobicity or modified crosslink density. The multi-functional amine is capable of inducing gelation when mixed with an oxidized polysaccharide in an aqueous solution or dispersion. Suitable multi-functional amines include, but are not limited to, linear and branched diamines, such as diaminoalkanes, polyaminoalkanes, and spermine; branched polyamines, such as polyethylenimine; cyclic diamines, such as N,N'-bis(3-aminopropyl)piperazine, 5-amino-1,3,3-trimethylcyclohexanemethylamine, 1,3-bis(aminomethyl)cyclohexane, 1,4-diaminocyclohexane, and p-xylylenediamine; aminoalkyltrialkoxysilanes, such as 3-aminopropyltrimethoxysilane and 3-aminopropyltriethoxysilane; aminoalkyldialkoxyalkylsilanes, such as 3-aminopropyldiethoxymethylsilane, dihydrazides, such as adipic dihydrazide; linear polymeric diamines, such as linear polyethylenimine, α,ω-amino-terminated polyethers, α,ω-bis(3-aminopropyl)polybutanediol, β,ω-1-amino-terminated polyethers (linear Jeffamines®); comb polyamines, such as chitosan, polyallylamine, and polylysine, and di- and polyhydrazides, such as bis(carboxyhydrazido)polyethers and poly(carboxyhydrazido) star polyethers. Many of these compounds are commercially available from companies such as Sigma-Aldrich and Huntsman LLC. Typically, if present, the multi-functional amine is used at a concentration of about 5% by weight to about 1000% by weight relative to the weight of the multi-arm amine in the aqueous solution or dispersion.

In another embodiment, the multi-functional amine is provided in a separate third solution at a concentration of about 5% by weight to about 100% by weight relative to the total weight of the solution. If the multi-functional amine is not used neat (i.e., 100% by weight), it is used in the form of an aqueous solution or dispersion. For use on living tissue, it is preferred that the solution comprising the multi-functional amine be sterilized. Any of the methods described above for sterilizing the first and second aqueous solutions or dispersions may be used. The aqueous solution or dispersion comprising the multi-functional amine may further comprise various additives. Any of the additives described above may be used.

The first aqueous solution or dispersion and the second aqueous solution or dispersion may be applied to an anatomical site in the body of humans or animals in any number of ways. The anatomical site may be any external or internal part of the body of humans or animals, including but not limited to, tissues, organs, lumens, or voids. Once both solutions or dispersions are applied to a site, they crosslink to form a hydrogel, a process referred to herein as curing, typically in about 1 second to about 2 minutes. The first aqueous solution or dispersion and the second aqueous solution or dispersion may be applied to an anatomical site such as a tissue or organ to form a hydrogel coating on the site. Additionally, the two aqueous solutions may be applied to an anatomical site such as a lumen or void to form a hydrogel which completely or partially blocks or fills the lumen or void.

In one embodiment, the two aqueous solutions or dispersions are applied to the site sequentially using any suitable means including, but not limited to, spraying, brushing with a cotton swab or brush, or extrusion using a pipette, or a syringe. The solutions or dispersions may be applied in any order. Then, the solutions or dispersions are mixed on the site using any suitable device, such as a cotton swab, a spatula, or the tip of the pipette or syringe.

In another embodiment, the two aqueous solutions or dispersions are mixed manually before application to the site. The resulting mixture is then applied to the site before it completely cures using a suitable applicator, as described above.

In another embodiment, the two aqueous solutions or dispersions are contained in separate barrels of a double-barrel syringe. In this way the two aqueous solutions or dispersions are applied simultaneously to the site with the syringe. Suitable double-barrel syringe applicators are known in the art. For example, Redl describes several suitable applicators for use in the invention in U.S. Pat. No. 6,620,125, (particularly FIGS. 1, 5, and 6, which are described in Columns 4, line 10 through column 6, line 47). Additionally, the double barrel syringe may contain a motionless mixer, such as that available from ConProtec, Inc. (Salem, N.H.) or Mixpac Systems AG (Rotkreuz, Switzerland), at the tip to effect mixing of the two aqueous solutions or dispersions prior to application. Alternatively, the mixing tip may be equipped with a spray head, such as that described by Cruise et al. in U.S. Pat. No. 6,458,147. Additionally, the mixture of the two aqueous solutions or dispersions from the double-barrel syringe may be applied to the site using a catheter or endoscope. Devices for mixing a two liquid component tissue adhesive and delivering the resulting mixture endoscopically are known in the art and may be adapted for the mixing and delivery of the two aqueous solutions or dispersions disclosed herein (see for example, Nielson, U.S. Pat. No. 6,723,067; and Redl et al., U.S. Pat. No. 4,631,055).

In another embodiment, the first aqueous solution or dispersion and the second aqueous solution or dispersion are applied to the site simultaneously where they mix to form a hydrogel. The two aqueous solutions or dispersions may be applied to the site in various ways, for example, using a dual-lumen catheter, such as those available from Bistech, Inc. (Woburn, Mass.). Additionally, injection devices for introducing two liquid components endoscopically into the body simultaneously are known in the art and may be adapted for the delivery of the two aqueous solutions or dispersions disclosed herein (see for example, Linder et al., U.S. Pat. No. 5,322,510).

In another embodiment, the two aqueous solutions or dispersions may be applied to the site using a spray device, such as those described by Fukunaga et al. (U.S. Pat. No. 5,582,596), Delmotte et al. (U.S. Pat. No. 5,989,215) or Sawhney (U.S. Pat. No. 6,179,862).

In another embodiment, the two aqueous solutions or dispersions may be applied to the site using a minimally invasive surgical applicator, such as those described by Sawhney (U.S. Pat. No. 7,347,850).

In another embodiment, the high swell, long-lived hydrogel sealant disclosed herein is used to bond at least two anatomical sites together. In this embodiment, the first aqueous solution or dispersion is applied to at least one site, and the second aqueous solution or dispersion is applied to at least one of either the same site or one other site. The two or more sites are contacted and held together manually or using some other means, such as a surgical clamp, for a time sufficient for the mixture to cure, typically from about 1 second to about 2 minutes. Alternatively, a mixture of the two aqueous solutions or dispersions either premixed manually or using a double-barrel syringe applicator, is applied to at least one of the anatomical sites to be bonded. The two or more sites are contacted and held together manually or using some other means, such as a surgical clamp, for a time sufficient for the mixture to cure.

In another embodiment, the high swell, long-lived hydrogel sealant disclosed herein is used in the form of a dried hydrogel. In this embodiment, a hydrogel is prepared by mixing a first solution or dispersion comprising at least one highly oxidized polysaccharide containing aldehyde groups in a first solvent with a second solution or dispersion comprising at least one multi-arm amine in a second solvent, to form the hydrogel. The first solvent may be either the same as or different from the second solvent. If two different solvents are used to prepare the first solution or dispersion and the second solution or dispersion, the two solvents are miscible with each other. Suitable solvents include, but are not limited to, water, ethanol, isopropanol, tetrahydrofuran, hexanes, and polyethylene glycol. In one embodiment, both the first solvent and the second solvent are water.

For the reasons discussed above, where the concentration of the highly oxidized polysaccharide in the first solution or dispersion used to prepare the dried hydrogel is equal to or greater than 5 wt % but less than 6 wt %, the equivalent weight per aldehyde group of the highly oxidized polysaccharide is about 80 to about 85 Daltons in order to obtain a crosslink density that results in a hydrogel with high swell. Where the concentration of the highly oxidized polysaccharide in the first solution or dispersion is equal to or greater than 3 wt % but less than 5 wt %, the equivalent weight per aldehyde group of the highly oxidized polysaccharide is about 65 to about 85 Daltons. The second solution or dispersion used to prepare the dried hydrogel contains the multi-arm amine at a concentration of about of 5% to about 70% by weight, more particularly about 15% to about 50% by weight, more particularly about 30% to about 50% by weight, relative to the total weight of the solution or dispersion.

The solutions or dispersions used to prepare the dried hydrogel may further comprise various additives depending on the intended application. Any of the additives described above may be used. The hydrogel is then treated to remove at least a portion of the solvent(s) contained therein to form the dried hydrogel. Preferably, substantially all of the solvent(s) is/are removed from the hydrogel. The solvent(s) may be removed from the hydrogel using methods known in the art, for example, using heat, vacuum, a combination of heat and vacuum, or flowing a stream of dry air or a dry inert gas such as nitrogen over the hydrogel. The dried hydrogel may be sterilized using the methods described above.

In one embodiment, the dried hydrogel is used in the form of a film. The dried hydrogel film may be formed by casting a mixture of the first and second solutions or dispersions, as described above, on a suitable substrate and treating the resulting hydrogel to form a dried hydrogel film. The dried hydrogel film may be applied directly to an anatomical site. Additionally, the dried hydrogel film may be used to bond two anatomical sites together.

In another embodiment, the dried hydrogel is used in the form of finely divided particles. The dried hydrogel particles may be formed by comminuting the dried hydrogel using methods known in the art, including, but not limited to, grinding, milling, or crushing with a mortar and pestle. The dried hydrogel particles may be applied to an anatomical site in a variety of ways, such as sprinkling or spraying, and may also be used to bond two anatomical sites together.

Kits

In one embodiment, the kit comprises at least one highly oxidized polysaccharide having an equivalent weight per aldehyde group of about 65 to about 85 Daltons contained in a first aqueous solution or dispersion at a concentration of greater than or equal to about 3% but less than 6% by weight, and at least one multi-arm amine contained in a second aqueous solution or dispersion, as described above. Each of the aqueous solutions or dispersions may be contained in any suitable vessel, such as a vial or a syringe barrel.

In another embodiment, the kit comprises a dried hydrogel comprising a highly oxidized polysaccharide and a multi-arm amine, prepared as described above. The dried hydrogel may be a film, finely divided particles, or other dried forms. The kit may further comprise a buffer for hydrating the dried hydrogel. The dried hydrogel may be contained in any suitable container.

Medical Applications

The high swell, long-lived hydrogel sealant disclosed herein may be particularly suitable for applications requiring high swell and slow degradation including, but not limited to, tissue augmentation, both cosmetic and reconstructive; void filling; tissue bulking, for example treatment of urinary incontinence and acid reflux; and embolization. The high swell, long-lived hydrogel sealant may also be useful as a tissue sealant and adhesive, and as an anti-adhesion barrier. In these applications the first aqueous solution or dispersion and the second aqueous solution or dispersion, or the dried hydrogel may be applied to the desired anatomical site using the methods described above.

For example, augmentation of skin tissues, including fascia, subcutaneous and dermal tissues, may be used to treat skin disorders including scars, skin laxness, and skin thinning, and may be used in some types of cosmetic and reconstructive plastic surgery. Such disorders of the skin often are exhibited as contour deficiencies, which may be treated using the high swell, long-lived hydrogel disclosed herein. Contour deficiencies in the skin can occur as a result of factors such as aging, environmental exposures, weight loss, child-bearing, surgery or disease. Contour deficiencies include frown lines, worry lines, wrinkles, crow's feet, marionette lines, stretch marks, and internal and external scars. Augmentation of the skin layers may reduce or eliminate contour deficiencies. To augment skin tissues, the first aqueous solution or dispersion and the second aqueous solution or dispersion or a mixture thereof may be injected into the desired skin layer, using the methods described above, where they react to form a hydrogel. The high swell, long-lived hydrogel will then augment the skin layer to modify the contour of the skin.

Medical situations may result in the occurrence of voids in either intra-organ or extra-organ locations, or there may be natural voids requiring treatment due to a medical condition. The high swell of the hydrogel disclosed herein may make it suitable as a material to be used in void filling treatments. For example, in intestinal diverticular disease, an intestinal diverticulum forms, which is a small outpouching in a weakened area of the bowel wall. When present, an intestinal diverticulum can become inflamed as a result of fecal trapping in the pouch, and can also hemorrhage. A treatment for this situation is to fill the outpouching thereby eliminating the trapping of material and reducing the risk of hemorrhage.

Extra-organ voids may be formed following surgical excision of soft tissue or organs such as in the case of partial lung resections, hysterectomies, mastectomies, or bowel excisions. The vacant spaces that are created by removal of these organs fill with fluid and debris, creating mechanical compromise and elevating risk of infection. A treatment for this situation is to use a mechanical bulking agent to fill the extra-organ space (Giudicelli et al. (1979) *Annales de Chirurgie* 33(3):151-154). In this application, the first aqueous solution or dispersion and the second aqueous solution or dispersion or a mixture thereof may be injected into the extra-organ space (including the pleura, pericardium, or peritoneum) using a double barrel syringe or dual-lumen catheter, as described herein, to form a hydrogel which will fill the extra-organ space.

In addition voids may be created by surgical procedures such as a biopsy, removal of a tumor, tooth extraction, or removal of infected or damaged tissue. In any of these cases the void may be filled through the use of the high swell, long-lived hydrogel, as described above. Filling such voids may reduce the incidence of infection and minimize abnormal appearance of external tissue.

Tissue bulking is another medical treatment which may be used in a variety of situations, and which may benefit from the application of the high swell, long-lived hydrogel disclosed herein. Tissue bulking may be used as a treatment for disorders such as sphincter weakness, dermal scarring, loss of skin tone, gum degeneration, and other situations where there is thinning or degeneration of tissues. The high swell of the hydrogel disclosed herein may make it an effective material for use in tissue bulking. For example, the high swell, long-lived hydrogel may be used as a bulking agent to treat gastroesophageal reflux disease (GERD). GERD is the return of the stomach's acidic contents back up into the esophagus. In normal digestion, the lower esophageal sphincter opens to allow food to pass into the stomach and closes to prevent food and acidic stomach juices from flowing back into the esophagus. GERD occurs when the lower esophageal sphincter is weak or relaxes, allowing stomach contents to flow up into the esophagus. A treatment for this condition is to use a bulking agent to provide physical support to the lower esophageal sphincter (Ozawa et al. (2005) *Annals of Thoracic and Cardiovascular Surgery* 11(3):146-153). In this application, the first aqueous solution or dispersion and the second aqueous solution or dispersion or a mixture thereof may be injected directly into the lower esophageal sphincter. The hydrogel that forms will swell, providing increased bulk at the injection site, which in turn provides the sphincter muscles with additional capability to control flow of digested food.

The high swell, long-lived hydrogel may also be used as a bulking agent to treat urinary incontinence, particularly, female stress urinary incontinence. Stress urinary incontinence is the loss of urine from the bladder caused by pressure occurring during activities such as exercise, coughing, and sneezing. One cause of this problem is the weakening of the urethral sphincter, a ring-shaped muscle at the base of the bladder that controls the flow of urine. A remedy for this condition is to use a bulking agent to provide physical support to the urethral sphincter (Madjar et al. (2003) *Journal of Urology* 170(6 Pt 1):2327-2329). In this application, the first aqueous solution or dispersion and the second aqueous solution or dispersion or a mixture thereof may be injected directly into the urinary sphincter. The hydrogel that forms will swell, providing increased bulk at the injection site, which in turn provides the sphincter muscles with additional capability to control urine flow.

Embolization treatment involves the introduction of a material into the vasculature in order to block the blood flow in a particular region. This procedure may be used to treat non-cancerous tumors, such as uterine fibroids, and cancerous tumors. Vascular occlusion in the case of tumors may be used to suppress pain, limit blood loss during surgery, or to cause tumor necrosis. In addition, embolization treatment may be used to control bleeding caused by conditions such as stomach ulcers, aneurysms, and injury. Treatment of arteriovenous malformation (AVM), where abnormal connections occur between arteries and veins, may also be through embolization to block blood flow. To effect embolization, the first aqueous solution or dispersion and the second aqueous solution or dispersion, or a mixture thereof may be applied into the vasculature of a mammal where they will crosslink in situ to form a hydrogel. Once formed, the hydrogel should effectively block the blood flow distal to the occlusion site. The occlusion site may be any target site where, for medical treatment, it is desired to block the flow of blood. For example, the occlusion site may be in a blood vessel that feeds a tumor such as a uterine fibroid or a cancerous tumor, in an arteriovenous malformation, or in a blood vessel where the blood is not contained, such as in the case of a stomach ulcer or injury. Preoperative embolization may also be performed to stop blood flow to a region targeted for surgery. The first aqueous solution or dispersion and the second aqueous solution or dispersion may be applied into the vasculature of a mammal in a variety of ways. The amount of the material introduced depends on a number of variables, such as the size of the blood vessel to be occluded, and may be determined by one skilled in the art using routine experimentation. Because the components are both liquids, they can be delivered readily to small blood vessels; however, large blood vessels may be effectively occluded as well. In one embodiment, the first aqueous solution or dispersion and the second aqueous solution or dispersion are premixed and the resulting mixture is introduced into the vasculature using methods known in the art. For example, the two aqueous solutions or dispersions may be premixed using a double barrel syringe equipped with a mixing tip, such as that available form ConProtec, Inc. (Salem, N.H.) or Mixpac Systems AG (Rotkreuz, Switzerland), and introduced into the vasculature using a catheter or endoscope. Additionally, devices for mixing a two liquid component tissue adhesive and delivering the resulting mixture endoscopically are known in the art and may be adapted for the mixing and delivery of the two liquid components disclosed herein (see for example, Nielson, U.S. Pat. No. 6,723,067; and Redl et al., U.S. Pat. No. 4,631,055). Alternatively, the first aqueous solution or dispersion and the second aqueous solution or dispersion, may be applied into the vasculature simultaneously where they mix to form a hydrogel which should occlude the blood vessel. The two liquids may be introduced into the vasculature in various ways, for example, using a dual-lumen catheter, as described above. Additionally, injection devices for introducing two liquid components endoscopically into the body simultaneously are known in the art and may be adapted for the delivery of the two liquid components disclosed herein (see for example, Linder et al., U.S. Pat. No. 5,322,510).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "sec" means second(s), "d" means day(s), "mL" means milliliter(s), "L" means liter(s), "µL" means microliter(s), "cm" means centimeter(s), "mm" means millimeter(s), "µm" means micrometer(s), "mol" means mole(s), "mmol" means millimole(s), "g" means gram(s), "mg" means milligram(s), "kg" means kilogram(s), "wt %" means percent by weight, "mol %" means mole percent, "M" means molar concentration, "Vol" means volume, "v/v" means volume per volume, "Da" means Dalton(s), "kDa" means kiloDalton(s), "mw" means molecular weight, the designation "10K" means that a polymer molecule possesses a weight-average molecular weight of about 10 kiloDaltons, a designation of "60K" indicates a weight-average molecular weight of about 60 kiloDaltons, etc., "MWCO" means molecular weight cut-off, "Pa" means pascal(s), "kPa" means kilopascal(s), "PBS" means phosphate-buffered saline, "PEG" means polyethylene glycol, "rpm" means revolutions per minute.

A reference to "Aldrich" or a reference to "Sigma" means the said chemical or ingredient was obtained from Sigma-Aldrich, St. Louis, Mo.

All water used in these Examples was doubly distilled unless otherwise stated.

General Methods:

Preparation of Highly Oxidized Dextrans:

Preparation of the following highly oxidized dextrans, also referred to herein as dextran aldehydes, is described below: (1) D450-77 (the first number is the approximate weight-average molecular weight of the dextran in kDa and the second number is the equivalent weight per aldehyde group of the highly oxidized dextran) having 87% oxidation conversion (equivalent weight per aldehyde group of 77 Daltons) from dextran having a weight-average molecular weight of 400 to 500 kDa, (2) D10-73 having 91 % oxidation conversion (equivalent weight per aldehyde group of 73 Daltons) from dextran having a weight-average molecular weight of 8,500 to 11,500 Da, and (3) D60-77 having 87% oxidation conversion (equivalent weight per aldehyde group of 77 Daltons) from dextran having a weight-average molecular weight of 60,000 to 90,000 Da. Oxidized dextrans of the same average molecular weights having other oxidation conversions were prepared by varying the amount of the sodium periodate used. For example, the following dextran aldehydes were also prepared: weight-average molecular weight of 8,500-11,500 Da with an oxidation conversion of 50%, equivalent weight per aldehyde group of about 146 Da (D10-146); weight-average molecular weight of 8,500-11,500 Da with an oxidation conversion of 90%, equivalent weight per aldehyde group of about 74 Da (D10-74); weight-average molecular weight of 8,500-11,500 Da with an oxidation conversion of 84%, equivalent weight per aldehyde group of about 80 Da (D10-80); weight-average molecular weight of 8,500-11,500 Da with an oxidation conversion of 76%, equivalent weight per aldehyde group of about 91 Da (D10-91); weight-average molecular weight of 60,000-90,000 Da with an oxidation conversion of 85%, equivalent weight per aldehyde group of about 79 Da (D60-79); weight-average molecular weight of 60,000-90,000 Da with an oxidation conversion of 93%, equivalent weight per aldehyde group of about 71 Da (D60-71); and weight-average molecular weight of 60,000-90,000 Da with an oxidation conversion of 50%, equivalent weight per aldehyde group of about 146 Da (D60-146).

Preparation of Oxidized Dextran D450-77:

In a round bottom flask, 15 g of dextran (weight-average molecular weight of 400 to 500 kDa, Sigma D1037) was dissolved in 135 mL of water. Then, a sodium periodate solution (30.5 g in 200 mL of water) was added to the flask. The reaction mixture was stirred at room temperature for 5 h. After this time, the solution was removed from the round bottom flask, divided into four equal volumes and dispensed into 4 dialysis membrane tubes (MWCO=3500 Da). The tubes were dialyzed in water with 6 water exchanges. The dialysates were combined, and freeze dried.

The oxidation conversion was determined by $^1$H NMR from the ratio (R) of the integral of the $O_2$CH-region (from 6.3 ppm to 4.2 ppm minus the water peak) versus the integral of the —OCH-region (from 4.2 ppm to 3 ppm). The calculation is as follows:

Degree of unoxidized glucose units $(X)=(300R-300)/(3+2R)$

% of oxidation$=(100-100X)$

Using this method, the oxidation conversion was found to be 87%, equivalent weight per aldehyde group of about 77 Daltons.

Preparation of Oxidized Dextran D10-73:

In a round bottom flask, 20 g of dextran (weight-average molecular weight of 8,500 to 11,500 Daltons, Sigma D9260) was dissolved in 180 mL of water. Sodium periodate solution (41.1 g in 360 mL of water) was added to the round bottom flask. The reaction mixture was stirred at room temperature for 5 h, and then dialyzed in water (MWCO 3500 dialysis membrane tube, 6 water exchanges). The dialysates were combined, and freeze dried to yield 13.1 g of white solid.

The oxidation conversion was determined by $^1$H NMR to be 91%, equivalent weight per aldehyde group of about 73 Daltons. The oxidized dextran was analyzed by size exclusion chromatography: $M_w=9.9\times10^3$, $M_w/M_n=1.9$.

Preparation of Oxidized Dextran D60-77:

In a round bottom flask, 20 g of dextran (weight-average molecular weight of 60,000 to 90,000 Daltons, Sigma D3759) was dissolved in 180 mL of water. Sodium periodate solution (41.1 g in 360 mL of water) was added to the round bottom flask. The reaction mixture was stirred at room temperature for 5 h, and then dialyzed in water (MWCO 3500 dialysis membrane tube, 6 water exchanges). The dialysates were combined, and freeze dried to yield 15.6 g of white solid.

The oxidation conversion was determined by $^1$H NMR to be 87%, equivalent weight per aldehyde group of about 77 Daltons. The oxidized dextran was analyzed by size exclusion chromatography: $M_w=1.1\times10^5$, $M_w/M_n=6.6$.

Preparation of Multi-Arm PEG Amines:

Preparation of 8-Arm Polyethylene Glycol 10K Octaamine (P8-10-1):

An 8-arm PEG 10K octaamine, referred to herein as "P8-10-1," was synthesized using the two-step procedure described by Chenault in co-pending and commonly owned U.S. Patent Application Publication No. 2007/0249870. A typical synthesis is described here. In the first step, the 8-arm PEG 10K is converted to an 8-Arm PEG 10K chloride by reaction with thionyl chloride, i.e.,

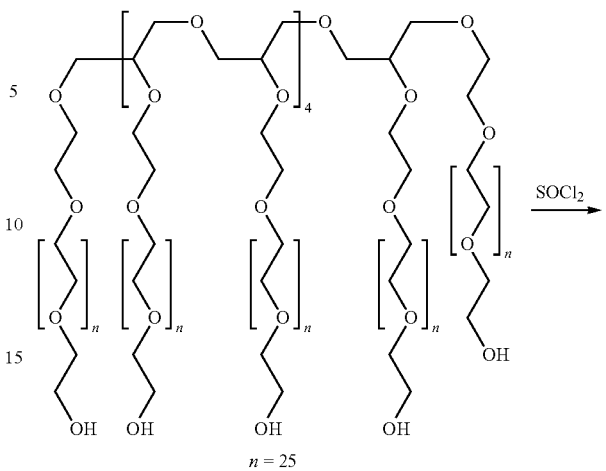

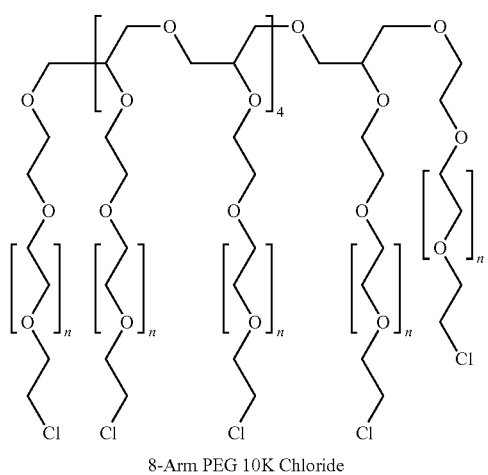

8-Arm PEG 10K Chloride

The 8-arm PEG 10K (NOF Sunbright HGEO-10000, NOF Corp., Tokyo, Japan; 1000 g in a 3-L round-bottom flask) is dried by dissolving it in 1.5 L of toluene and distilling 500 mL of toluene-water azeotrope plus toluene under reduced pressure (2 kPa) with a pot temperature of 60° C., adding another 500 mL of toluene to the pot, and distilling 500 mL of toluene-water azeotrope plus toluene under reduced pressure (2 kPa) with a pot temperature of 60° C.

The solution of 8-arm PEG is allowed to cool to room temperature. Then, thionyl chloride (233 mL, 3.19 mol) is added to the flask, which is equipped with a reflux condenser, and the mixture is heated at 85° C. with stirring under a blanket of nitrogen for 4 h. Excess thionyl chloride and most of the toluene are removed by vacuum distillation at 2 kPa (bath temp 40-60° C.). Two successive 500-mL portions of toluene are added and evaporated under reduced pressure (2 kPa, bath temperature 80-85° C.) to complete the removal of thionyl chloride. The final crude product is dissolved in 1000 g of de-ionized water.

In the second step, the 8-Arm PEG 10K chloride is converted to the 8-Arm PEG 10K amine by reaction with aqueous ammonia, i.e.,

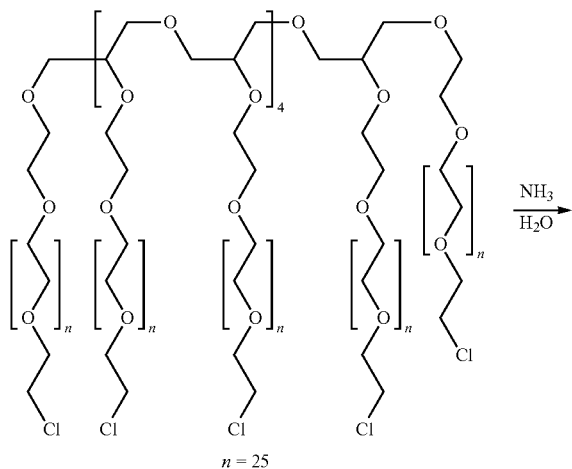

8-Arm PEG 10K Amine

The aqueous solution of 8-arm PEG-Cl prepared above, is dissolved in 16 L of concentrated aqueous ammonia (28 wt %) and heated in a sealed stainless steel pressure vessel at 60° C. for 48 h. The solution is sparged for 24 h with dry nitrogen and then placed under reduced pressure for 3 h to drive off ammonia. The solution is then passed through a column of strongly basic anion exchange resin (5 kg; PUROLITE® A-860, The Purolite Co., Bala-Cynwyd, Pa.) in the hydroxide form. The eluant is collected, and two 7-L portions of de-ionized water are passed through the column and collected. The aqueous fractions are combined, concentrated under reduced pressure (2 to 0.3 kPa, bath temperature 60° C.) to give the 8-Arm PEG 10K octaamine (P8-10-1). The final product is characterized by proton NMR and size exclusion chromatography (SEC), as described by Chenault, supra.

Preparation of 8-Arm PEG 40K Hexadecaamine (P8-40-2):

An 8-arm PEG 40K hexadecaamine, referred to herein as "P8-40-2," was prepared using a similar procedure as described above for the 8-arm PEG 10K octaamine, except that the 8-arm PEG chloride formed in the first step was reacted with tris(2-aminoethyl)amine to give the 8-arm PEG 40K hexadecaamine. A typical synthesis is described here.

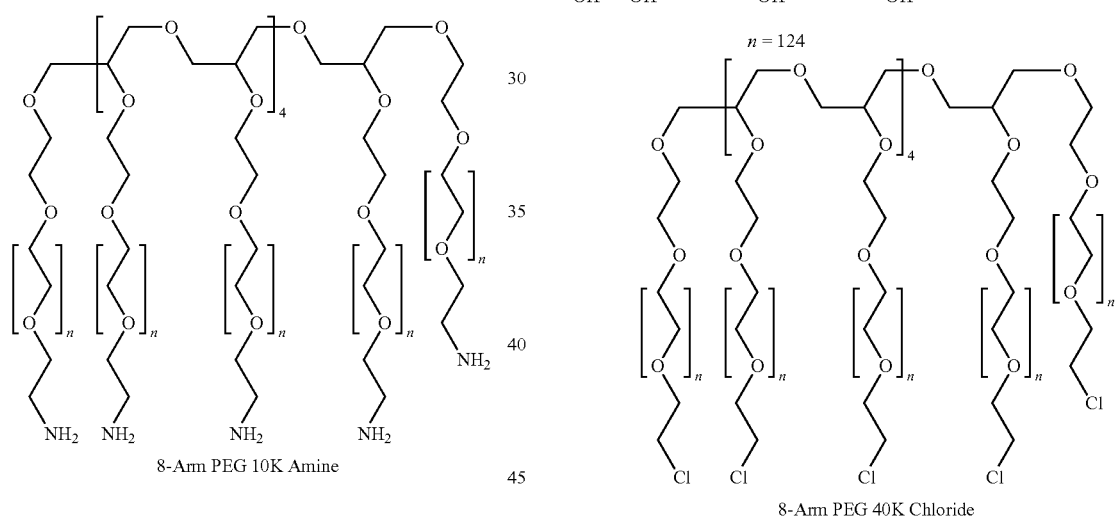

8-Arm PEG 40K Chloride

The 8-arm PEG 40K (NOF Sunbright HGEO-40000; 1000 g in a 4-L resin kettle) is dried by dissolving it in 1.5 L of toluene and distilling 500 mL of toluene-water azeotrope plus toluene under reduced pressure with a pot temperature of 70-80° C. After the distillation, the vacuum is broken with nitrogen, and 1.5 g (20 mmol) of N,N-dimethylformamide is added. Then, thionyl chloride (59 mL, 0.80 mol) is added to the reactor, which is equipped with a reflux condenser, and the mixture is heated at 85° C. with stirring under a blanket of nitrogen for 4 h. The reaction mixture is diluted with 1 L of toluene, held at 60-70° C., and then transferred into a 12-L, round-bottom flask equipped with an overhead stirrer and containing 4 L of heptane. The mixture is stirred under nitrogen and allowed to cool to room temperature. The resulting slurry is filtered, and the recovered solids are washed with 500 mL of heptane and then dried with aspiration under a flow of dry nitrogen to give the 8-arm PEG 40K chloride.

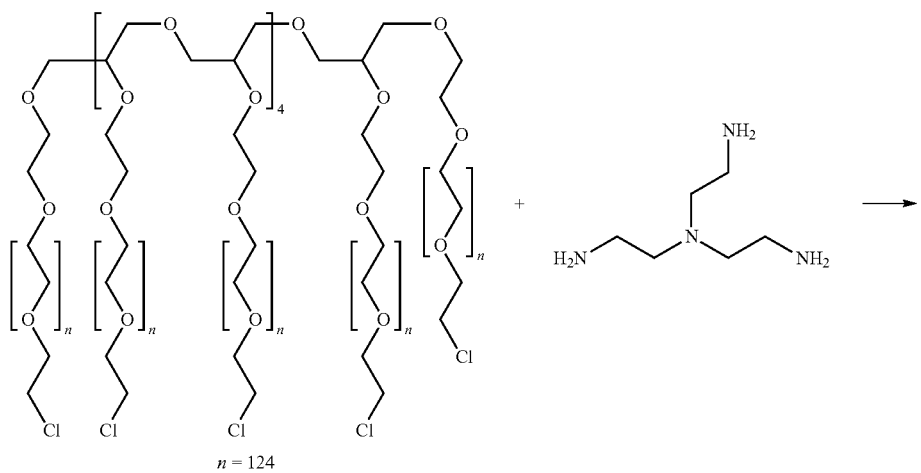

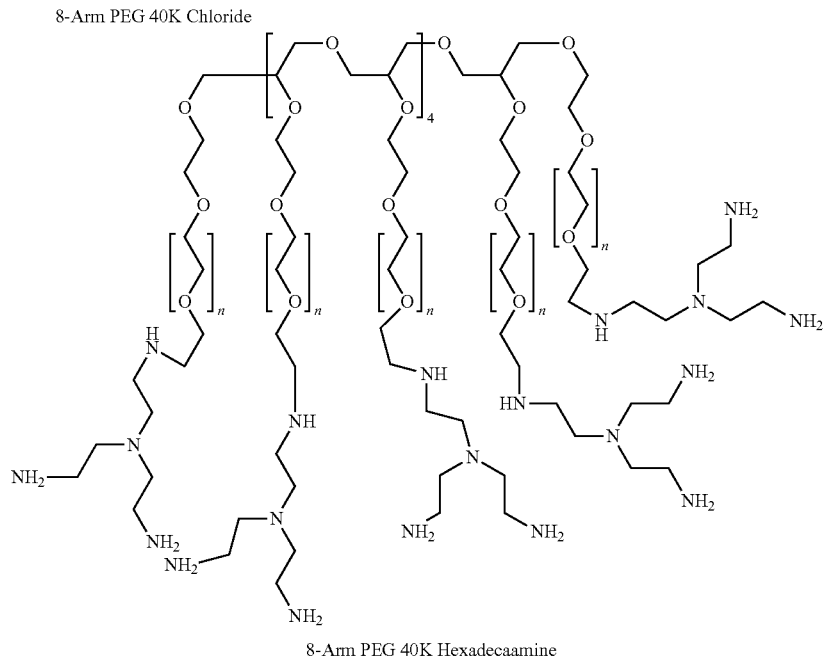

8-Arm PEG 40K Hexadecaamine

A 12-L, 4-neck round-bottom flask equipped with a mechanical stirrer and reflux condenser is charged with 993 g of 8-arm star PEG 40K chloride and 2000 mL of water. The mixture is heated to 90° C. with stirring to dissolve the PEG chloride. Then, 1200 mL (8.0 mol) of tris(2-aminoethyl) amine (TCI America, Portland, Oreg.; #T1243) is added. The reaction mixture is stirred at 100° C. for 8 h and then allowed to cool to room temperature overnight under nitrogen. The solution is transferred to a 20-L vessel under nitrogen and extracted with 10 L of dichloromethane. The organic layer is collected, dried over sodium sulfate with stirring under nitrogen, and then filtered through a pad of CELITE® diatomaceous earth (World Minerals, Lompoc, Calif.). The solution is concentrated to about 2 L and poured slowly with stirring into a 20-L vessel containing 10 L of methyl t-butyl ether. The resulting slurry is cooled to 0° C. and then filtered. The recovered solids are washed with 1.0 L of cold methyl t-butyl ether and then dried under vacuum to give the 8-arm PEG 40K hexadecaamine (P8-40-2). The final product is characterized by proton NMR and size exclusion chromatography (SEC), as described by Chenault, supra.

EXAMPLES 1-7

Preparation of High Swell, Long-Lived Hydrogels by Reaction of Highly Oxidized Dextrans with Multi-Arm PEG Amines The purpose of these Examples was to demonstrate the preparation of hydrogels from reaction of multi-arm PEG amine(s) with a highly oxidized dextran. The gel time to form the hydrogels was measured.

Into a small vial, 100 µL of an aqueous dextran aldehyde stock solution, as given in Table 1, was added. The vial was tilted and 100 µL of an aqueous solution containing a multi-arm PEG amine, prepared as described in General Methods, was added with care taken not to mix the two solutions. A timer was started and the two solutions were stirred together with the wooden end of a cotton swab. The initial gel time was defined as the observation of increased viscosity, such that a string formed when the wooden stirring rod was pulled from the gel. The final gel time was defined as the second when stirring pulled the gel from the sides of the vial so that the gel could be removed as the wooden stirring rod was pulled from the vial.

The initial and final gel times are given in Table 1. The results demonstrate that the reaction of multi-arm PEG amines with highly oxidized dextran aldehydes produces hydrogels with a final gel time ranging from 3 to 6 sec, depending on the concentration and oxidation conversion of the dextran aldehyde used.

TABLE 1

Gel Times for Forming Hydrogels Prepared from Highly Oxidized Dextrans and Multi-Arm PEG Amines

| Example | Dextran Aldehyde Solution | PEG Amine Solution | Initial Gel Time (sec) | Final Gel Time (sec) |
|---|---|---|---|---|
| 1 | D10-73 4 wt % | P8-10-1 50 wt % | 1-2 | 4 |
| 2 | D60-77 4 wt % | P8-10-1 50 wt % | 1 | 5 |
| 3 | D450-77 4 wt % | P8-10-1 50 wt % | 1 | 3 |
| 4 | D450-77 4 wt % | P8-10-1 30 wt % | 2 | 5 |
| 5 | D10-73 4 wt % | P8-10-1/ P8-40-2 (4:1) 50 wt % | 1-2 | 5 |
| 6 | D60-77 4 wt % | P8-10-1/ P8-40-2 (4:1) 50 wt % | 2 | 6 |
| 7 | D450-77 4 wt % | P8-10-1/ P8-40-2 (4:1) 50 wt % | 2 | 4 |

EXAMPLES 8-21

In Vitro Degradation of Hydrogels—Comparison at the Same Solids Content

The purpose of these Examples was to demonstrate that the hydrogels formed by reaction of a highly oxidized dextran aldehyde with a multi-arm PEG amine degrade in vitro much more slowly than a hydrogel formed from a less oxidized dextran aldehyde and a multi-arm PEG amine, at the same solids content.

The hydrogel samples were prepared by mixing equal volumes of an aqueous solution of a dextran aldehyde and an aqueous solution of a multi-arm PEG amine, as shown in Table 2. After the hydrogels cured, the samples were weighed and placed inside jars containing PBS (phosphate buffered saline) at pH 7.4. The jars were placed inside a temperature-controlled shaker set at 80 rpm and 37° C. The samples were removed from the jars at various times, blotted to remove excess solution, and weighed. Then, the samples were returned to the jars.

The results are summarized in Table 2. The degradation day is defined as the day when the gel was dissolved. The maximum swell reported in the table is the maximum weight of the hydrogel measured during the course of the study divided by the initial weight of the hydrogel, multiplied by 100.

TABLE 2

Results of In Vitro Degradation of Hydrogels

| Example | Dextran Aldehyde Solution | PEG Amine Solution | Maximum Swell (%) | Degradation (Days) |
|---|---|---|---|---|
| 8, Comparative | D10-146 4 wt % | P8-10-1 50 wt % | 133 | 0.1 |
| 9 | D10-74 4 wt % | P8-10-1 50 wt % | 635 | >5 |
| 10 | D10-80 4 wt % | P8-10-1 50 wt % | 400 | 5 |
| 11, Comparative | D10-91 4 wt % | P8-10-1 50 wt % | 134 | 1 |
| 12, Comparative | D10-146 4 wt % | P8-10-1 30 wt % | 100 | <1 |
| 13 | D10-74 4 wt % | P8-10-1 30 wt % | 352 | >29 |
| 14 | D10-80 4 wt % | P8-10-1 30 wt % | 368 | >18 |
| 15, Comparative | D60-146 4 wt % | P8-10-1 50 wt % | 100 | <1 |
| 16 | D60-71 4 wt % | P8-10-1 50 wt % | 300 | >29 |
| 17, Comparative | D60-146 4 wt % | P8-10-1 30 wt % | 100 | <1 |
| 18 | D60-71 4 wt % | P8-10-1 30 wt % | 461 | >22 |
| 19 | D60-79 4 wt % | P8-10-1 30 wt % | 456 | >22 |
| 20 | D450-77 4 wt % | P8-10-1 50 wt % | 444 | >29 |
| 21 | D450-77 4 wt % | P8-10-1 30 wt % | 356 | >29 |

As can be seen from the data in Table 2, hydrogels formed from highly oxidized dextran had much longer degradation times while maintaining high swell characteristics than hydrogels formed from dextran aldehyde having a lower oxidation level (i.e., Comparative Examples 8, 11, 12, 15, and 17 at the same solids content.

EXAMPLES 22-23

In Vitro Biocompatibility Testing—Cytotoxicity

The purpose of these Examples was to demonstrate the safety of hydrogels resulting from the reaction of a multi-arm PEG amine with a highly oxidized dextran aldehyde in an in vitro test.

The testing was done using NIH3T3 mouse fibroblast cell cultures according to ISO 10993-5:1999. The NIH3T3 mouse fibroblast cells were obtained from the American Type Culture Collection (ATCC; Manassas, Va.) and were grown in Dulbecco's modified essential medium (DMEM), supplemented with 10% fetal calf serum.

NIH3T3 mouse fibroblast cell cultures were challenged with hydrogels made by combining equal volumes of an aqueous solution of a highly oxidized-dextran aldehyde and an aqueous solution of a multi-arm PEG amine, as shown in Table 3. Each hydrogel was placed in a well in a polystyrene culture plate such that about ¼ of the well bottoms were covered. The wells were then sterilized under UV light and seeded with 50,000-100,000 NIH3T3 cells.

The cells grew normally confluent and coated the well bottom, growing up to the edges of the hydrogels; however, they did not overgrow the hydrogels. These results, summarized in Table 3, demonstrate a lack of cytotoxicity of the hydrogels, as well as the lack of adhesion of cell cultures to the hydrogels.

TABLE 3

Cytotoxicity Results

| Example | Dextran Aldehyde Solution | Multi-Arm PEG Amine Solution | Cytotoxicity |
|---|---|---|---|
| 22 | D10-73 4 wt % | P8-10-1 50 wt % | nontoxic |
| 23 | D60-77 4 wt % | P8-10-1 50 wt % | nontoxic |

EXAMPLES 24 AND 25

In-Vitro Burst Testing of a Sealed Scalpel Incision in Swine Uterine Horn

The purpose of these Examples was to demonstrate the burst strength of a seal made with various hydrogels of an incision made in the uterine horn from a swine.

A syringe pump system was used to measure the burst strength of a seal of an incision made in a section of uterine horn from a pig. The syringe pump (Model No. 22, Harvard Apparatus, Holliston, Mass.) was modified to be equipped with two 30 mL syringes, which were connected together through a "Y" junction. Water was pumped through a single piece of TYGON® R-36 tubing (0.6 cm diameter) and through a pressure gauge (Model PDG 5000L, Omega Engineering, Stamford, Conn.).

An approximately 12.5 cm section of clean pig intestine, obtained from a local abattoir, was fitted on one end with a metal plug with a feed line fitting for water feed from the syringe pump and on the other end with a metal plug with a threaded hole which could be sealed with a machine screw. The plugs were held in place with nylon ties around the outside of the intestine. An incision was made through the intestine wall into the interior by puncturing with a BARD PARKER™ surgical blade handle 5 (obtained from BD Surgical Products, Franklin Lakes, N.J.), fitted with a #15 surgical blade. The incision on the outside of the intestine was wider than the scalpel blade (typically 4-5 mm) while the hole through the inside wall was about 3 mm (about equal to the blade). This size incision mimics the distance between the interrupted sutures if an intestine were to be cut and later sutured. The intestine was filled with water containing a purple dye via the syringe pump until water began to leak from the open hole in the end plug and also from the scalpel puncture in the intestinal wall. The pump was then turned off and the end plug was sealed with the machine screw. The scalpel incision site was blotted dry using a paper towel.

The dextran aldehyde and multi-arm PEG amine solutions were prepared in water. The two solutions were applied to the incision using a double barrel syringe (Mixpac Systems AG (Rotkreuz, Switzerland) fitted with a 16 step static mixer (Mixpac Systems AG). After the application, the adhesive was allowed to cure at room temperature for no longer than 2 min.

Burst pressure testing, also referred to herein as leak pressure testing, was done by pressurizing the sealed uterine horn with water from the syringe pump at a flow rate of 11 mL/min until the bioadhesive seal began to leak, at which point the pressure was recorded. Adhesive failure was attributed when the water leaked under the seal between the hydrogel and the tissue surface. Cohesive failure was attributed when the water penetrated and leaked through the hydrogel itself. Burst pressure testing was also done on the unsealed uterine horn and the leak pressure was less than 10 mm of mercury (Hg) (less than 1.3 kPa).

The results of the burst testing are summarized in Table 4. The results demonstrate that the hydrogel formed by reaction of highly oxidized dextran aldehyde and multi-arm PEG amine solutions (i.e., Example 25) was able to seal the incision in the swine uterine horn and gave a higher burst pressure than the hydrogel prepared from oxidized dextran aldehyde having a lower oxidation level and a multi-arm PEG amine (i.e., Comparative Example 24) at the same solids content.

TABLE 4

Burst Pressure Testing Results

| Example | Dextran Aldehyde Solution | Multi-Arm PEG Amine Solution (P8-10-1) | Ave Burst Pressure, mm Hg | Standard Deviation Burst Pressure, mm Hg |
|---|---|---|---|---|
| 24, Comparative | D10-146 4 wt % | 50 wt % | 13.1 (1.75 kPa) | 2.44 (0.32 kPa) |
| 25 | D10-73 4 wt % | 50 wt % | 111.9 (14.9 kPa) | 29.6 (3.9 kPa) |

EXAMPLES 26 AND 27

Tensile Strength Testing

The purpose of these Examples was to demonstrate the tensile strength of a hydrogel formed by reaction of a highly oxidized dextran aldehyde with a multi-arm PEG amine.

The hydrogel samples were prepared by mixing equal volumes of an aqueous solution of a dextran aldehyde and an aqueous solution of a multi-arm PEG amine, as shown in Table 5. Tensile strength testing was done using the following method.

A 1:1 v/v double-barrel syringe (Mixpac Systems AG, Rotkreuz, Switzerland) was loaded with the two reactive solutions, dextran aldehyde solution in one side and a multi-arm PEG amine solution in the other. The syringe was fitted with a 2.5-mm diameter mixing tip having 16 static mixing elements (Mixpac No. 2.5-16-DM) to dispense sealant. Two 1 inch×3 inch (2.5 cm×7.5 cm) microscope slides were laid parallel to one another, exactly 0.68 cm apart using a spacer, on a sheet of silicone rubber which had been lightly rubbed with silicone stopcock grease as a release agent. A bead of mixed sealant solution was quickly delivered onto the silicone rubber surface between the two slides and promptly covered with a 5 cm×7.5 cm microscope slide to compress the still-fluid sealant to a flat strip between the two slides. The strip was allowed to cure for 15 min; then the silicone sheet was carefully peeled away, leaving the hydrogel strip on the glass slide. The two 1 inch×3 inch (2.5 cm×7.5 cm) slides were carefully removed and finally the adhering hydrogel strip was carefully peeled off the 5 cm×7.5 cm microscope slide. Sample strips were tested immediately after molding. If there were no flaws or bubbles, the strip could be cut in the center to give two test pieces, each approximately 3 cm long.

Tensile strength was determined using an Exceed Texture Analyzer (Stable Microsystems, Surrey, England) with clamps for pulling films. Pieces of smooth silicone rubber sheet were taped with double-sided tape onto the clamp faces to lightly grip the hydrogels without squashing them. The hydrogel strips were clamped with a gauge length of 1.00 cm (about 1 cm of each end of the 3-cm hydrogel strip was in each clamp) and pulled at a rate of 1 cm/min for 10 cm or until break. After break, the thickness of the hydrogel strip at the break point was measured with a micrometer to calculate tensile strength.

The results are summarized in Table 5. The results demonstrate that the hydrogel comprised of a highly oxidized dextran aldehyde (i.e., Example 27) had a greater tensile strength than the hydrogel formed using dextran aldehyde having a lower oxidization level (i.e., Comparative Examples 26) at the same solids content.

TABLE 5

Results of Tensile Strength Testing

| Example | Dextran Aldehyde Solution | PEG Amine Solution (P8-10-1) | Tensile Strength (g/cm$^2$) |
|---|---|---|---|
| 26, Comparative | D10-146 4 wt % | 50 wt % | 401 |
| 27 | D10-73 4 wt % | 50 wt % | 2647 |

What is claimed is:

1. A kit for preparing a high swell, long-lived sealant comprising:
   a) a first aqueous solution or dispersion comprising at least one highly oxidized polysaccharide containing aldehyde groups, said highly oxidized polysaccharide having a weight-average molecular weight of about 1,000 to about 1,000,000 Daltons and an equivalent weight per aldehyde group of about 65 to about 85 Daltons, wherein said first aqueous solution or dispersion contains said highly oxidized polysaccharide at a concentration of greater than or equal to about 3% but less than 6% by weight; and
   b) a second aqueous solution or dispersion comprising at least one water-dispersible, multi-arm amine wherein at least three of the arms are terminated by at least one primary amine group, said multi-arm amine having a number-average molecular weight of about 450 to about 200,000 Daltons, wherein said second aqueous solution or dispersion contains said multi-arm amine at a concentration of about 5% to about 70% by weight;
   wherein the high swell, long-lived sealant is formed when
   (i) the concentration of the highly oxidized polysaccharide in the first aqueous solution or dispersion is equal to or greater than 5 wt % but less than 6 wt %, the equivalent weight per aldehyde group of the highly oxidized polysaccharide is about 80 to about 85 Daltons; or
   (ii) the concentration of the highly oxidized polysaccharide in the first aqueous solution or dispersion is equal to or greater than 3 wt % but less than 5 wt %, the equivalent weight per aldehyde group of the highly oxidized polysaccharide is about 65 to about 85 Daltons.

2. The kit according to claim 1 wherein the polysaccharide is selected from the group consisting of dextran, starch, agar, cellulose, and hyaluronic acid.

3. The kit according to claim 1 wherein the water-dispersible, multi-arm amine is selected from the group consisting of amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star polyethylene oxide-polypropylene oxide copolymers, amino-terminated dendritic polyethylene oxide-polypropylene oxide copolymers, amino-terminated comb polyethylene oxide-polypropylene oxide copolymers, polyoxyalkylene triamines, amino-terminated dendritic polyamidoamines, and multi-arm branched end amines.

4. The kit according to claim 1 wherein the polysaccharide is dextran and the water-dispersible, multi-arm amine is a multi-arm polyethylene glycol amine.

5. The kit according to claim 1 further comprising at least one multi-functional amine having one or more primary amine groups, wherein said multi-functional amine is contained in at least one of the following:
   a) the first aqueous solution or dispersion;
   b) the second aqueous solution or dispersion;
   c) a third solution.

6. A dried hydrogel for preparing a high swell, long-lived sealant, the dried hydrogel formed by a process comprising the steps of:
   a) combining (i) a first solution or dispersion comprising at least one highly oxidized polysaccharide containing aldehyde groups in a first solvent, said oxidized polysaccharide having a weight-average molecular weight of about 1,000 to about 1,000,000 Daltons and an equivalent weight per aldehyde group of about 65 to about 85 Daltons, said first solution or dispersion containing said highly oxidized polysaccharide at a concentration of greater than or equal to about 3% but less than 6% by weight; with (ii) a second solution or dispersion comprising at least one water-dispersible, multi-arm amine in a second solvent, wherein at least three of the arms of the multi-arm amine are terminated by at least one primary amine group, said multi-arm amine having a number-average molecular weight of about 450 to about 200,000 Daltons, wherein said second solution or dispersion contains said multi-arm amine at a concentration of about 5% to about 70% by weight, to form a hydrogel, wherein the first solvent is either the same as or different from the second solvent; and
   b) treating the hydrogel to remove at least a portion of said first solvent and said second solvent to form the dried hydrogel;
   wherein the high swell, long-lived sealant is formed when
   (i) the concentration of the highly oxidized polysaccharide in the first solution or dispersion is equal to or greater than 5 wt % but less than 6 wt %, the equivalent weight per aldehyde group of the highly oxidized polysaccharide is about 80 to about 85 Daltons; or
   (ii) the concentration of the highly oxidized polysaccharide in the first solution or dispersion is equal to or greater than 3 wt % but less than 5 wt %, the equivalent weight per aldehyde group of the highly oxidized polysaccharide is about 65 to about 85 Daltons.

7. The dried hydrogel according to claim 6 wherein said dried hydrogel is in the form of a film.

8. The dried hydrogel according to claim 6 wherein the process further comprises the step of comminuting the dried hydrogel to form finely divided particles.

9. The dried hydrogel according to claim 6 wherein the polysaccharide is selected from the group consisting of dextran, starch, agar, cellulose, and hyaluronic acid.

10. The dried hydrogel according to claim 6 wherein the water-dispersible, multi-arm amine is selected from the group consisting of amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star polyethylene oxide-polypropylene oxide copolymers, amino-terminated dendritic polyethylene oxide-polypropylene oxide copolymers, amino-terminated comb polyethylene oxide-polypropylene oxide copolymers, polyoxyalkylene triamines, amino-terminated dendritic polyamidoamines, and multi-arm branched end amines.

11. The dried hydrogel according to claim 6 wherein the polysaccharide is dextran and the multi-arm amine is a multi-arm polyethylene glycol amine.

12. The dried hydrogel according to claim 6 wherein the first solvent and the second solvent are water.

13. A method for applying a coating comprising a high swell long-lived sealant to an anatomical site on tissue of a living organism comprising: applying to the site
  (a) a first aqueous solution or dispersion comprising at least one highly oxidized polysaccharide containing aldehyde groups, said highly oxidized polysaccharide having a weight-average molecular weight of about 1,000 to about 1,000,000 Daltons and an equivalent weight per aldehyde group of about 65 to about 85 Daltons, wherein said first aqueous solution or dispersion contains said highly oxidized polysaccharide at a concentration of greater than or equal to about 3% but less than 6% by weight; followed by (b) a second aqueous solution or dispersion comprising at least one water-dispersible, multi-arm amine wherein at least three of the arms are terminated by at least one primary amine group, said multi-arm amine having a number-average molecular weight of about 450 to about 200,000 Daltons, wherein said second aqueous solution or dispersion contains said multi-arm amine at a concentration of about 5% to about 70% by weight, or
  applying (b) followed by (a) and mixing (a) and (b) on the site, or
  premixing (a) and (b) to form a mixture and applying said mixture to the site;
  wherein the high swell, long-lived sealant is formed when
    (i) the concentration of the highly oxidized polysaccharide in the first aqueous solution or dispersion is equal to or greater than 5 wt % but less than 6 wt %, the equivalent weight per aldehyde group of the highly oxidized polysaccharide is about 80 to about 85 Daltons; or
    (ii) the concentration of the highly oxidized polysaccharide in the first aqueous solution or dispersion is equal to or greater than 3 wt % but less than 5 wt %, the equivalent weight per aldehyde group of the highly oxidized polysaccharide is about 65 to about 85 Daltons.

14. The method according to claim 13 wherein the polysaccharide is dextran and the multi-arm amine is a multi-arm polyethylene glycol amine.

15. A method for completely or partially blocking or filling a lumen or void within the body of humans or animals comprising the steps of: applying into said lumen or void (a) a first aqueous solution or dispersion comprising at least one highly oxidized polysaccharide containing aldehyde groups, said highly oxidized polysaccharide having a weight-average molecular weight of about 1,000 to about 1,000,000 Daltons and an equivalent weight per aldehyde group of about 65 to about 85 Daltons, wherein said first aqueous solution or dispersion contains said highly oxidized polysaccharide at a concentration of greater than or equal to about 3% but less than 6% by weight; followed by (b) a second aqueous solution or dispersion comprising at least one water-dispersible, multi-arm amine wherein at least three of the arms are terminated by at least one primary amine group, said multi-arm amine having a number-average molecular weight of about 450 to about 200,000 Daltons, wherein said second aqueous solution or dispersion contains said multi-arm amine at a concentration of about 5% to about 70% by weight, or
  applying (b) followed by (a), or applying (a) and (b) simultaneously or
  premixing (a) and (b) to form a mixture and applying said mixture to the lumen or void;
  wherein a high swell, long-lived sealant is formed when
    (i) the concentration of the highly oxidized polysaccharide in the first aqueous solution or dispersion is equal to or greater than 5 wt % but less than 6 wt %, the equivalent weight per aldehyde group of the highly oxidized polysaccharide is about 80 to about 85 Daltons; or
    (ii) the concentration of the highly oxidized polysaccharide in the first aqueous solution or dispersion is equal to or greater than 3 wt % but less than 5 wt %, the equivalent weight per aldehyde group of the highly oxidized polysaccharide is about 65 to about 85 Daltons.

16. The method according to claim 15 wherein the polysaccharide is dextran and the water-dispersible, multi-arm amine is a multi-arm polyethylene glycol amine.

17. A composition comprising the reaction product of:
  a) a first aqueous solution or dispersion comprising at least one highly oxidized polysaccharide containing aldehyde groups, said highly oxidized polysaccharide having a weight-average molecular weight of about 1,000 to about 1,000,000 Daltons and an equivalent weight per aldehyde group of about 65 to about 85 Daltons, wherein said first aqueous solution or dispersion contains said highly oxidized polysaccharide at a concentration of greater than or equal to about 3% but less than 6% by weight; and
  b) a second aqueous solution or dispersion comprising at least one water-dispersible, multi-arm amine wherein at least three of the arms are terminated by at least one primary amine group, said multi-arm amine having a number-average molecular weight of about 450 to about 200,000 Daltons, wherein said second aqueous solution or dispersion contains said multi-arm amine at a concentration of about 5% to about 70% by weight;
  wherein a high swell, long-lived sealant is formed when
    (i) the concentration of the highly oxidized polysaccharide in the first aqueous solution or dispersion is equal to or greater than 5 wt % but less than 6 wt %, the equivalent weight per aldehyde group of the highly oxidized polysaccharide is about 80 to about 85 Daltons; or
    (ii) the concentration of the highly oxidized polysaccharide in the first aqueous solution or dispersion is equal to or greater than 3 wt % but less than 5 wt %, the equivalent weight per aldehyde group of the highly oxidized polysaccharide is about 65 to about 85 Daltons.

18. The composition according to claim 17 wherein the polysaccharide is selected from the group consisting of dextran, starch, agar, cellulose, and hyaluronic acid.

19. The composition according to claim 17 wherein the water-dispersible multi-arm amine is selected from the group consisting of amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star polyethylene oxide-polypropylene oxide copolymers, amino-terminated dendritic polyethylene oxide-polypropylene oxide copolymers, amino-terminated comb polyethylene oxide-polypropylene oxide copolymers, polyoxyalkylene triamines, amino-terminated dendritic polyamidoamines, and multi-arm branched end amines.

20. The composition according to claim 17 wherein the polysaccharide is dextran and the water-dispersible, multi-arm amine is a multi-arm polyethylene glycol amine.

* * * * *